US012569245B2

(12) United States Patent
Comee et al.

(10) Patent No.: US 12,569,245 B2
(45) Date of Patent: *Mar. 10, 2026

(54) SUTURE BASED CLOSURE DEVICE

(71) Applicant: BOSTON SCIENTIFIC SCIMED, INC., Maple Grove, MN (US)

(72) Inventors: Shaun D. Comee, Fiskdale, MA (US); Dennis B. Hubbard, Jr., Lancaster, MA (US); Jason R. Lebeau, Bridgewater, MA (US); Norman C. May, Valrico, FL (US); Paul Smith, Smithfield, RI (US); Robert B. DeVries, Northborough, MA (US); Christopher R. Deuel, Melrose, MA (US); Stan Robert Gilbert, Litchfield, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 121 days.

This patent is subject to a terminal disclaimer.

(21) Appl. No.: 18/383,300

(22) Filed: Oct. 24, 2023

(65) Prior Publication Data

US 2024/0050085 A1     Feb. 15, 2024

Related U.S. Application Data

(63) Continuation of application No. 17/130,500, filed on Dec. 22, 2020, now Pat. No. 11,832,809, which is a
(Continued)

(51) Int. Cl.
A61B 17/04     (2006.01)
A61B 1/00     (2006.01)
(Continued)

(52) U.S. Cl.
CPC ............ *A61B 17/0469* (2013.01); *A61B 1/00* (2013.01); *A61B 1/00087* (2013.01);
(Continued)

(58) Field of Classification Search
CPC ....... A61B 1/00; A61B 1/00087; A61B 1/018; A61B 17/0469; A61B 17/0482;
(Continued)

(56) References Cited

U.S. PATENT DOCUMENTS 5,478,344 A     12/1995     Stone
5,584,861 A     12/1996     Swain et al.
(Continued)

FOREIGN PATENT DOCUMENTS

CA         2682488 A1     10/2008
DE     202005022017 U1     5/2012
(Continued)

OTHER PUBLICATIONS

International Search Report and Written Opinion dated Aug. 20, 2019 for International Application No. PCT/US2019/033748.
(Continued)

*Primary Examiner* — Mohamed G Gabr
(74) *Attorney, Agent, or Firm* — Seager, Tufte & Wickhem, LLP

(57)     ABSTRACT

A suture device may include a suture translation assembly configured to be axially translatable within a lumen of a delivery system and a distal assembly configured to be securable to the distal end of the delivery system. The suture translation assembly and the distal assembly may cooperate to enable a user to pass a needle back and forth between the two in order to endoscopically suture a defect.

20 Claims, 49 Drawing Sheets

Related U.S. Application Data continuation of application No. 15/901,477, filed on Feb. 21, 2018, now Pat. No. 10,932,771.

(60) Provisional application No. 62/477,250, filed on Mar. 27, 2017, provisional application No. 62/461,969, filed on Feb. 22, 2017.

(51) Int. Cl.

| | |
|---|---|
| *A61B 1/018* | (2006.01) |
| *A61B 17/00* | (2006.01) |
| *A61B 17/06* | (2006.01) |
| *A61B 17/062* | (2006.01) |

(52) U.S. Cl.
CPC .......... *A61B 1/018* (2013.01); *A61B 17/0482* (2013.01); *A61B 17/06166* (2013.01); *A61B 17/0625* (2013.01); *A61B 2017/00296* (2013.01); *A61B 2017/00349* (2013.01); *A61B 2017/00477* (2013.01); *A61B 2017/00663* (2013.01); *A61B 2017/0496* (2013.01); *A61B 2017/06047* (2013.01); *A61B 2017/0609* (2013.01)

(58) Field of Classification Search
CPC .......... A61B 17/06166; A61B 17/0625; A61B 2017/00296; A61B 2017/00349; A61B 2017/00477; A61B 2017/00663; A61B 2017/0496; A61B 2017/06047; A61B 2017/0609

See application file for complete search history.

(56) References Cited

U.S. PATENT DOCUMENTS

| | | | |
|---|---|---|---|
| 6,086,608 | A | 7/2000 | Ek et al. |
| 6,200,329 | B1 | 3/2001 | Fung et al. |
| 6,494,888 | B1 | 12/2002 | Laufer et al. |
| 6,506,196 | B1 | 1/2003 | Laufer |
| 6,554,845 | B1 | 4/2003 | Fleenor et al. |
| 6,569,085 | B2 | 5/2003 | Kortenbach et al. |
| 6,626,917 | B1 | 9/2003 | Craig |
| 6,663,639 | B1 | 12/2003 | Laufer et al. |
| 6,719,763 | B2 | 4/2004 | Chung et al. |
| 6,740,030 | B2 | 5/2004 | Martone et al. |
| 6,746,457 | B2 | 6/2004 | Dana et al. |
| 6,755,843 | B2 | 6/2004 | Chung et al. |
| 6,773,441 | B1 | 8/2004 | Laufer et al. |
| 6,808,491 | B2 | 10/2004 | Kortenbach et al. |
| 6,821,285 | B2 | 11/2004 | Laufer et al. |
| 6,835,200 | B2 | 12/2004 | Laufer et al. |
| 6,908,427 | B2 | 6/2005 | Fleener et al. |
| 6,997,931 | B2 | 2/2006 | Sauer et al. |
| 7,056,284 | B2 | 6/2006 | Martone et al. |
| 7,063,710 | B2 | 6/2006 | Takamoto et al. |
| 7,063,715 | B2 | 6/2006 | Onuki et al. |
| 7,094,246 | B2 | 8/2006 | Anderson et al. |
| 7,144,401 | B2 | 12/2006 | Yamamoto et al. |
| 7,147,646 | B2 | 12/2006 | Dana et al. |
| 7,153,314 | B2 | 12/2006 | Laufer et al. |
| 7,220,266 | B2 | 5/2007 | Gambale |
| 7,232,445 | B2 | 6/2007 | Kortenbach et al. |
| 7,235,086 | B2 | 6/2007 | Sauer et al. |
| 7,326,221 | B2 | 2/2008 | Sakamoto et al. |
| 7,344,545 | B2 | 3/2008 | Takemoto et al. |
| 7,347,863 | B2 | 3/2008 | Rothe et al. |
| 7,361,180 | B2 | 4/2008 | Saadat et al. |
| 7,530,985 | B2 | 5/2009 | Takemoto et al. |
| 7,601,161 | B1 | 10/2009 | Nobles et al. |
| 7,618,425 | B2 | 11/2009 | Yamamoto et al. |
| 7,713,277 | B2 | 5/2010 | Laufer et al. |
| 7,722,633 | B2 | 5/2010 | Laufer et al. |
| 7,727,246 | B2 | 6/2010 | Sixto, Jr. et al. |
| 7,736,373 | B2 | 6/2010 | Laufer et al. |

| | | | |
|---|---|---|---|
| 7,776,057 | B2 | 8/2010 | Laufer et al. |
| 7,776,066 | B2 | 8/2010 | Onuki et al. |
| 7,842,051 | B2 | 11/2010 | Dana et al. |
| 7,846,180 | B2 | 12/2010 | Cerier |
| 7,857,823 | B2 | 12/2010 | Laufer et al. |
| 7,896,893 | B2 | 3/2011 | Laufer et al. |
| 7,918,867 | B2 | 4/2011 | Dana et al. |
| 7,951,157 | B2 | 5/2011 | Gambale |
| 7,992,571 | B2 | 8/2011 | Gross et al. |
| 7,993,368 | B2 | 8/2011 | Gambale et al. |
| 8,016,840 | B2 | 9/2011 | Takemoto et al. |
| 8,021,376 | B2 | 9/2011 | Takemoto et al. |
| 8,057,494 | B2 | 11/2011 | Laufer et al. |
| 8,062,314 | B2 | 11/2011 | Sixto, Jr. et al. |
| 8,066,721 | B2 | 11/2011 | Kortenbach et al. |
| 8,105,355 | B2 | 1/2012 | Page et al. |
| 8,211,123 | B2 | 7/2012 | Gross et al. |
| 8,216,253 | B2 | 7/2012 | Saadat et al. |
| 8,226,667 | B2 | 7/2012 | Viola et al. |
| 8,277,468 | B2 | 10/2012 | Laufer et al. |
| 8,287,554 | B2 | 10/2012 | Cerier et al. |
| 8,287,556 | B2 | 10/2012 | Gilkey et al. |
| 8,308,765 | B2 | 11/2012 | Saadat et al. |
| 8,313,496 | B2 | 11/2012 | Sauer et al. |
| 8,361,089 | B2 | 1/2013 | Chu |
| 8,388,632 | B2 | 3/2013 | Gambale |
| 8,425,555 | B2 | 4/2013 | Page et al. |
| 8,454,631 | B2 | 6/2013 | Viola et al. |
| 8,480,691 | B2 | 7/2013 | Dana et al. |
| 8,540,735 | B2 | 9/2013 | Mitelberg et al. |
| 8,551,120 | B2 | 10/2013 | Gambale |
| 8,585,720 | B2 | 11/2013 | Gross et al. |
| 8,632,553 | B2 | 1/2014 | Sakamoto et al. |
| 8,679,136 | B2 | 3/2014 | Mitelberg |
| 8,709,022 | B2 | 4/2014 | Stone et al. |
| 8,764,771 | B2 | 7/2014 | Chu |
| 8,882,785 | B2 | 11/2014 | DiCesare et al. |
| 8,926,634 | B2 | 1/2015 | Rothe et al. |
| 8,992,570 | B2 | 3/2015 | Gambale et al. |
| 9,011,466 | B2 | 4/2015 | Adams et al. |
| 9,089,325 | B2 | 7/2015 | Mitelberg et al. |
| 9,125,646 | B2 | 9/2015 | Woodard, Jr. et al. |
| 9,198,562 | B2 | 12/2015 | Mitelberg et al. |
| 9,320,515 | B2 | 4/2016 | Dana et al. |
| 9,486,126 | B2 | 11/2016 | West et al. |
| 9,504,465 | B2 | 11/2016 | Chu |
| 9,510,817 | B2 | 12/2016 | Saadat et al. |
| 9,549,728 | B2 | 1/2017 | Chu |
| 9,750,494 | B2 | 9/2017 | Gross et al. |
| 9,788,831 | B2 | 10/2017 | Mitelberg |
| 9,844,366 | B2 | 12/2017 | Woodard, Jr. et al. |
| 9,867,610 | B2 | 1/2018 | Mitelberg et al. |
| 10,045,871 | B2 | 8/2018 | Saadat et al. |
| 10,143,463 | B2 | 12/2018 | Dana et al. |
| 10,194,902 | B2 | 2/2019 | Nobles et al. |
| 10,335,142 | B2 | 7/2019 | Raybin et al. |
| 10,932,771 | B2 * | 3/2021 | Comee ............. A61B 17/06166 |
| 11,832,809 | B2 * | 12/2023 | Comee ..................... A61B 1/00 |
| 2002/0107530 | A1 | 8/2002 | Sauer et al. |
| 2003/0195529 | A1 | 10/2003 | Takamoto et al. |
| 2003/0204205 | A1 | 10/2003 | Sauer et al. |
| 2004/0002699 | A1 | 1/2004 | Ryan et al. |
| 2004/0138706 | A1 | 7/2004 | Abrams et al. |
| 2005/0033319 | A1 | 2/2005 | Gambale et al. |
| 2005/0250985 | A1 | 11/2005 | Saadat et al. |
| 2006/0282094 | A1 | 12/2006 | Stokes et al. |
| 2007/0270908 | A1 | 11/2007 | Stokes et al. |
| 2008/0086148 | A1 | 4/2008 | Baker et al. |
| 2009/0177031 | A1 | 7/2009 | Surti et al. |
| 2010/0137681 | A1 | 6/2010 | Ewers et al. |
| 2010/0198006 | A1 | 8/2010 | Greenburg et al. |
| 2011/0276064 | A1 | 11/2011 | Henrichsen et al. |
| 2012/0158023 | A1 | 6/2012 | Miltelberg et al. |
| 2012/0271327 | A1 | 10/2012 | West et al. |
| 2012/0277768 | A1 * | 11/2012 | Viola ................. A61B 17/0469 |
| | | | 606/145 |
| 2013/0096581 | A1 | 4/2013 | Gilkey et al. |
| 2013/0304093 | A1 | 11/2013 | Serina et al. |
| 2014/0121457 | A1 | 5/2014 | Mort et al. |

(56) References Cited

U.S. PATENT DOCUMENTS

| 2014/0128668 | A1 | 5/2014 | Cox et al. |
| 2015/0126983 | A1 | 5/2015 | Alvarado et al. |
| 2016/0045197 | A1 | 2/2016 | Mitelberg et al. |
| 2017/0042534 | A1 | 2/2017 | Nobles et al. |
| 2017/0086817 | A1 | 3/2017 | Mitelberg |
| 2017/0086818 | A1 | 3/2017 | Mitelberg |
| 2017/0119371 | A1 | 5/2017 | Mims et al. |
| 2017/0319197 | A1 | 11/2017 | Gross et al. |
| 2018/0042602 | A1 | 2/2018 | Mitelberg et al. |
| 2018/0042603 | A1 | 2/2018 | Mitelberg et al. |
| 2018/0153381 | A1 | 6/2018 | Wei et al. |
| 2018/0221009 | A1 | 8/2018 | Mitelberg et al. |
| 2018/0235604 | A1 | 8/2018 | Comee et al. |
| 2018/0344501 | A1 | 12/2018 | Saadat et al. |
| 2020/0360011 | A1 | 11/2020 | Deuel et al. |

FOREIGN PATENT DOCUMENTS

| EP | 1354558 | A2 | 10/2003 |
| EP | 1520509 | A1 | 4/2005 |
| EP | 2108304 | A2 | 10/2009 |
| JP | 2003305046 | A | 10/2003 |
| JP | 2011509121 | A | 3/2011 |
| WO | 0101868 | A1 | 1/2001 |
| WO | 0189393 | A1 | 11/2001 |
| WO | 2008016592 | A2 | 2/2008 |
| WO | 2008045376 | A2 | 4/2008 |
| WO | 2008098124 | A1 | 8/2008 |
| WO | 2010036227 | A1 | 4/2010 |
| WO | 2010085793 | A2 | 7/2010 |
| WO | 2016200811 | A1 | 12/2016 |
| WO | 2017087856 | A1 | 5/2017 |
| WO | 2018156603 | A1 | 8/2018 |

OTHER PUBLICATIONS

International Search Report and Written Opinion dated Oct. 1, 2019 for International Application No. PCT/US2019/038006.

Invitation to Pay Additional Fees dated Sep. 26, 2019 for International Application No. PCT/US2019/037995.

International Search Report and Written Opinion dated Dec. 6, 2019 for International Application No. PCT/US2019/037995.

International Search Report and Written Opinion dated Nov. 18, 2019 for International Application No. PCT/US2019/049774.

International Search Report and Written Opinion dated Sep. 20, 2019 for International Application No. PCT/US2019/039312.

JP Office Action, JP Application No. 2021-053892, dated Jan. 25, 2022 (5 Pages).

International Search Report and Written Opinion dated May 22, 2018 for International Application No. PCT/US2018/018982 (12 pages).

Korean Intellectual Property Office, Office Action, KR Application No. 10-2019-7027516, dated Mar. 29, 2021 (11 pages).

* cited by examiner

250

130a

12

210

SUTURE BASED CLOSURE DEVICE

CROSS-REFERENCE TO RELATED APPLICATIONS

This application is a continuation of U.S. application Ser. No. 17/130,500, filed Dec. 22, 2020, which is continuation of U.S. application Ser. No. 15/901,477, filed Feb. 21, 2018, which claims priority under 35 U.S.C. § 119 to U.S. Provisional Application Ser. No. 62/461,969, filed Feb. 22, 2017, and which claims priority under 35 U.S.C. § 119 to U.S. Provisional Application Ser. No. 62/477,250, filed Mar. 27, 2017, the entireties of which applications are incorporated herein by reference.

TECHNICAL FIELD

The disclosure is directed to devices for suturing tissue and more particularly to devices that work with an endoscope or similar device for endoscopically suturing tissue.

BACKGROUND

A variety of endoscopic treatments may result in defects (or wounds) that are too large for hemostasis clips to easily bridge and thus help to close the defect. Examples of such endoscopic treatments include removal of large lesions, tunneling under the mucosal layer, full thickness removal of tissue, treating other organs by passing outside of the gastrointestinal tract, and repair of post-surgical issues such as post-surgical leaks, failing surgical staple lines and anastomotic leaks. Endoscopic treatments also include bariatric revision procedures. Of the known devices and methods for endoscopically closing large defects, each has certain advantages and disadvantages.

SUMMARY

The disclosure is directed to several alternative designs, materials and methods of devices for endoscopically closing large defects. In an example, a suture device for use in combination with a delivery system including a lumen extending through the delivery system includes a suture translation assembly that is configured to be axially translatable within the lumen of the delivery system and a distal assembly that is configured to be securable to the distal end of the delivery system. In some cases, the suture translation assembly may be considered to be an active suture translation assembly while the distal assembly may be considered to be a passive distal assembly. The suture translation assembly may move relative to the delivery system while the distal assembly remains stationary relative to the delivery system. The suture translation assembly includes a needle usable to carry a suture, a distal shuttle that is configured to releasably secure the needle. A user interface extends proximally from the distal shuttle and is configured to releasably secure the needle. The distal assembly includes an endcap that is configured to releasably engage and disengage the needle, the endcap configured to engage the needle when the needle is advanced distally into the endcap, and to release the needle when the needle is locked to the distal shuttle and the distal shuttle is withdrawn proximally. A guide member is configured to permit the suture translation assembly to extend through the guide member and to translate relative to the guide member.

Alternatively or additionally, the needle may include a distal region and a proximal region, the distal region including a distal detent for releasably engaging the endcap, the proximal region including a proximal detent for releasably engaging the distal shuttle.

Alternatively or additionally, the endcap may include a proximal needle opening that is configured to accommodate the needle when the needle is advanced distally into the endcap, the proximal needle opening aligned with a longitudinal axis of the needle, one or more securement openings that are arranged orthogonal to the proximal needle opening and one or more securements that are disposed within the securement openings and are configured to releasably engage the distal detent of the needle.

Alternatively or additionally, the one or more securement openings may comprise an aperture that tapers from a first diameter that is larger than a diameter of a securement disposed therein to a second diameter that is about equal in diameter to the diameter of the securement.

Alternatively or additionally, the distal assembly further includes a set screw opening that is orthogonal to the securement opening and a set screw threadedly engaged in the set screw opening such that the set screw adjustably engages the securement.

Alternatively or additionally, the set screw opening is disposed closer to the first diameter than to the second diameter.

Alternatively or additionally, the one or more securements may be spring-loaded.

Alternatively or additionally, the guide member may include a channel cut longitudinally into the guide member in order to accommodate a suture therethrough.

Alternatively or additionally, the distal shuttle may include a distal needle opening that is configured to accommodate the needle when the distal shuttle is advanced distally over the needle, the distal needle opening aligned with a longitudinal axis of the needle, one or more bearing ball openings that are arranged orthogonal to the distal needle opening such that the one or more bearing ball openings align with the proximal detent when the needle is secured to the distal shuttle and one or more bearing balls that are disposed within the one or more bearing ball openings and disposable within the proximal detent when the needle is secured to the distal shuttle.

Alternatively or additionally, the user interface may further include a member that is disposable over the distal shuttle and is movable between a locked position in which the needle is secured to the distal shuttle and an unlocked position in which the needle is releasable from the distal shuttle. The member may include one or more member openings smaller in diameter than the one or more bearing balls. When in the locked position, the one or more member openings may be misaligned with the one or more bearing ball openings such that the one or more bearing balls engage the proximal detent of the needle and when in the unlocked position, the one or more member openings may be aligned with the one or more bearing ball openings such that the one or more bearing balls can move radially outward a distance sufficient to permit the one or more bearing balls to clear the proximal detent of the needle.

Alternatively or additionally, the user interface may include a proximal handle, a translating handle disposed relative to the proximal handle and a cable extending distally from the translating handle to the member. Axial movement of the translating handle relative to the proximal handle may cause the member to translate relative to the distal shuttle.

Alternatively or additionally, the distal shuttle may further include an internal void and a member capture element slidingly disposed within the internal void, the cable secured to the member capture element and the member capture element secured to the member, such that axial movement of the translating handle relative to the proximal handle causes the member capture element to translate within the internal void and thus permit the member to translate relative to the distal shuttle.

Alternatively or additionally, the member may further include one or more member capture apertures disposed within the sleeve, and the member capture member may be secured to the member via a pin extending through the member capture apertures and through the member capture member.

Alternatively or additionally, the translating handle may have a neutral position.

Alternatively or additionally, moving the translating handle distally from the neutral position may cause the member to move to the locked position and moving the translating handle proximally from the neutral position may cause the member to move to the unlocked position.

Alternatively or additionally, the delivery system may include an endo scope and the lumen may be a working channel of the endo scope.

Alternatively or additionally, the distal shuttle may include an inner member that is configured to accommodate the needle and a locking member that is slidingly disposed over the inner member, the locking member movable between a locked configuration in which the needle is secured to the distal shuttle and an unlocked configuration in which the needle is released from the distal shuttle.

Alternatively or additionally, the inner member may include a plurality of arms that releasably engage a proximal detent in the needle.

Alternatively or additionally, when in the locked configuration, the locking member is in a position in which the locking member prevents radially outward movement of the plurality of arms, and when in the unlocked configuration, the locking member has been withdrawn proximally relative to the inner member such that the arms are able to move radially outwardly.

Alternatively or additionally, the locking member is coupled to a control member that extends proximally and allows the locking member to be translated distally and proximally relative to the inner member.

Alternatively or additionally, the distal shuttle may include an inner member that is configured to accommodate the needle and a locking member that is slidingly disposed over the inner member, the inner member including one or more slots, the locking member including one or more tabs that releasably extend through the slots in order to engage the proximal detent of the needle.

Alternatively or additionally, the distal shuttle is movable between a locked configuration in which the one or more tabs of the locking member extend through the one or more slots of the inner member and an unlocked configuration in which the tabs are forced distally of the one or more slots, thereby releasing the needle.

Alternatively or additionally, the inner member further includes a pin extending radially outwardly from the inner member, and the locking member further includes an elongate slot to accommodate the pin, the pin and the elongate slot in combination limiting relative translation between the inner member and the locking member.

In another example, a suture device for use in combination with an endoscope having a working channel and a distal end includes a translation assembly configured to be axially translatable within the working channel and a distal assembly configured to be securable to the distal end of the endoscope. The translation assembly includes a needle that is configured to carry a suture, a distal shuttle that is configured to releasably secure the needle and a sleeve that is disposable over the distal shuttle and is movable between a locked position in which the needle is secured to the distal shuttle and an unlocked position in which the needle is releasable from the distal shuttle. The distal assembly includes an endcap that is configured to engage the needle when the needle is advanced distally into the endcap and to release the needle when the needle is locked to the distal shuttle and the distal shuttle is withdrawn proximally.

Alternatively or additionally, the translation assembly may further include a user interface that extends proximally from the distal shuttle and sleeve and is configured to enable a user to move the sleeve between the locked position and the unlocked position.

Alternatively or additionally, the user interface may include a proximal handle and a translating handle that is disposed relative to the proximal handle and movable both distally and proximally from a neutral position and a cable extending distally from the translating handle to the sleeve. Axial movement of the translating handle relative to the proximal handle may cause the sleeve to translate relative to the distal shuttle.

Alternatively or additionally, moving the translating handle distally from the neutral position may cause the sleeve to move to the locked position and moving the translating handle proximally from the neutral position may cause the sleeve to move to the unlocked position.

Alternatively or additionally, translating the proximal handle distally may advance the distal shuttle and thus the needle towards the endcap and translating the proximal handle distally may withdraw the distal shuttle and thus the needle proximally away from the endcap.

Alternatively or additionally, the suture device may further include a flexible silicone tube that is configured to secure the distal assembly to the distal end of the endoscope.

Alternatively or additionally, the distal assembly may further comprise a side-saddled lumen attachment element that is configured to provide a side lumen extending through an aperture in the body of the distal assembly.

Alternatively or additionally, the side-saddled lumen attachment element may be pivotally attached to the aperture in the body of the distal assembly.

Alternatively or additionally, the distal assembly may further comprise a tissue release mechanism that may be pivotally secured relative to the distal assembly.

Alternatively or additionally, the distal assembly may be spring-loaded or actuated via a separate control wire.

Alternatively or additionally, the user interface may include a friction disk that is disposed between the proximal handle and the translating handle such that the friction disk resists relative movement between the proximal handle and the translating handle.

In another example, a suture device configured to be useable with a single channel endo scope may include an axially translatable needle assembly that includes a needle configured to carry a suture and that is configured to be translatable within the single channel and a distal assembly configured to be securable to the distal end of the single channel endoscope such that the axially translatable needle assembly can engage the distal assembly to pass the needle back and forth between engagement with the distal shuttle and engagement with the distal assembly. The translatable needle assembly includes a distal shuttle configured to releasably secure the needle and a sleeve that is disposable over the distal shuttle and is movable between a locked position in which the needle is secured to the distal shuttle and an unlocked position in which the needle is releasable from the distal shuttle. A cable is coupled with the distal shuttle and the sleeve and coaxially aligned with the distal shuttle and the sleeve. The suture device includes a proximal handle and a translating handle that is disposed relative to the proximal handle and secured to the cable and that is translatable to cause the sleeve to move between the locked position and the unlocked position.

Alternatively or additionally, translating the proximal handle distally may advance the distal shuttle and thus the needle towards the distal assembly and translating the proximal handle distally may withdraw the distal shuttle and thus the needle proximally away from the distal assembly.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The disclosure may be more completely understood in consideration of the following description of in connection with the accompanying drawings, in which.

Figure 1:
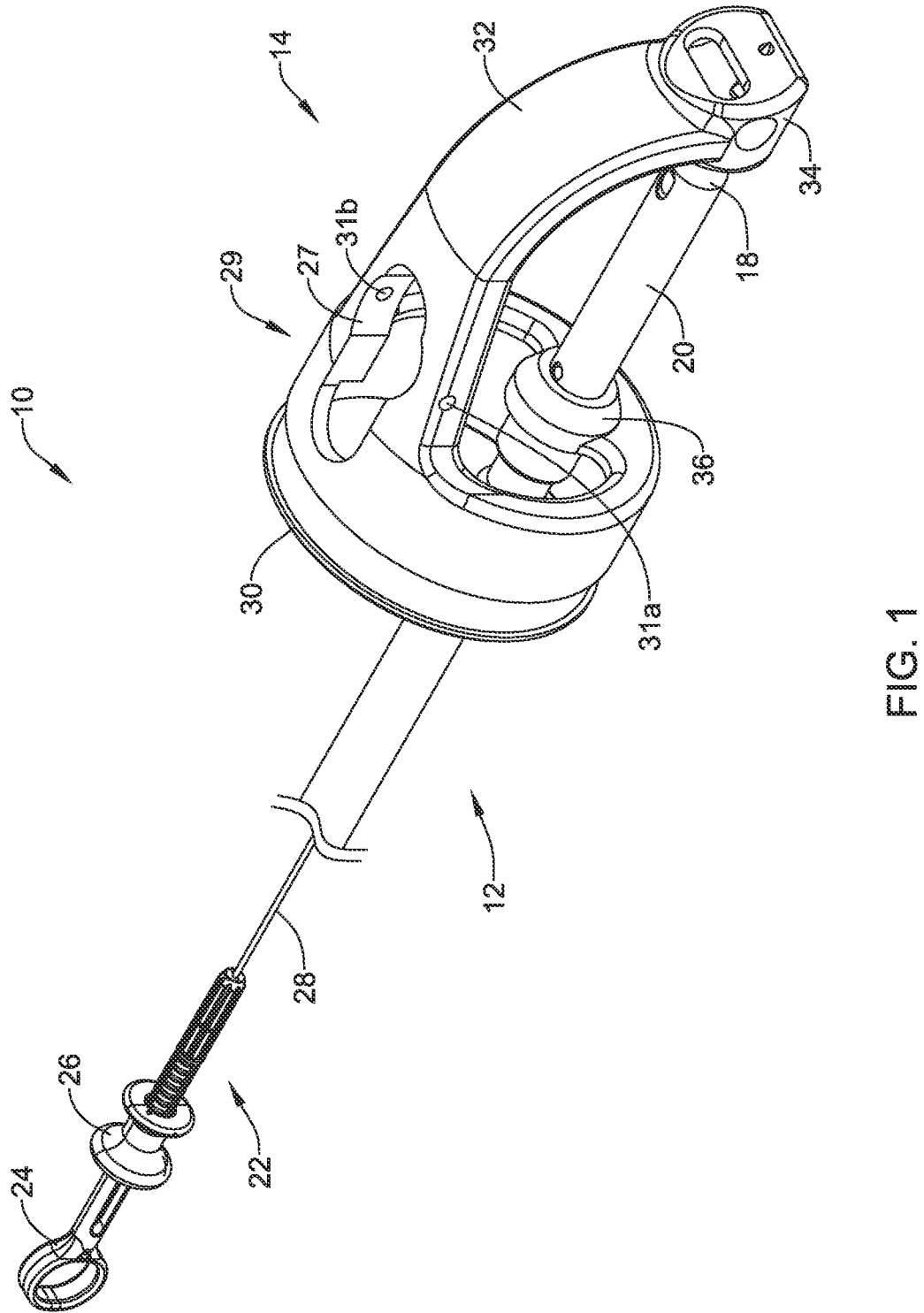
FIG. 1 is a perspective view of an illustrative suture device in accordance with an example of the disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

The disclosure pertains to devices that are configured to be used in combination with an endoscope or a similar delivery device for closing wounds within the body. In some instances, the suture devices described herein may be configured such that they may be used within a single working or available channel of an endoscope, and in some cases may be operated by a single individual, although in some cases a second individual may be involved. In some cases, the suture devices described herein may be considered as operating along a single line of operation. The device itself may be translatable distally and proximally within a working channel, and a handle portion may itself be translatable distally and proximally along the same line of operation in locking and unlocking a needle to be able to pass the needle back and forth between an active portion of the suture device and a passive portion of the suture device. The device may be configured to enable the needle to be selectively locked into either of a more distal position or a more proximal position, and the device may itself be translated distally or proximally with the needle locked in place in order to move the needle, and hence a suture, relative to the tissue being repaired.

FIG. 1 is a perspective view of a suture device 10 that may be considered as being configured for use in combination with a delivery system including a lumen that extends through the delivery system. For example, the delivery system may be an endoscope having a working channel. The delivery system may also be a catheter. It will be appreciated that there is a change in scale on either side of the break line shown. In some cases, the suture device 10 may be considered as including a suture translation assembly 12 that is configured to be axially translatable within the lumen of the delivery system and a distal assembly 14 that is configured to be secured to a distal end of the delivery system. The suture translation assembly 12 extends into the distal assembly 14 and includes a needle 16 that may be used to carry a suture as well as a distal shuttle 18 that is configured to releasably secure the needle 16.

A member 20 may be disposed over the distal shuttle 18 and, as will be shown in subsequent Figures, is movable between a locked position in which the needle 16 is secured to the distal shuttle 18 and an unlocked position in which the needle 16 is releasable from the distal shuttle 18. In some cases, for example, the member 20 may be a sleeve 20. A user interface 22 extends proximally from the distal shuttle 18 and the sleeve 20, and may be configured to move the sleeve 20 between the locked position and the unlocked position. In some cases, as shown, the user interface 22 may include a proximal handle 24 and a translating handle 26 that is disposed relative to the proximal handle 24. In some cases, as will be described, the proximal handle 24 may be used to move the suture device 10 proximally or distally, while the translating handle 26 may be used to move the needle 16 between the distal shuttle 18 and the distal assembly 14. A shaft 28 may extend distally from the proximal handle 24 to the suture translation assembly 12, and may in particular be coupled to the sleeve 20.

In some cases, the distal assembly 14 includes a body 29 having a proximal connector 30 that may be configured to be coupled to the distal end of an endoscope or other delivery system. The body 29 includes an arm 32 that extends to an endcap 34. As will be discussed, the endcap 34 may be configured to releasably engage and disengage the needle 16. In some cases, for example, the endcap 34 may be configured to engage the needle 16 when the needle 16 is advanced distally into the endcap 34, and to release the needle 16 when the needle 16 is locked into the distal shuttle 18 (as will be discussed) and the distal shuttle 18 is withdrawn proximally. The distal assembly 14 may be considered as including a guide member 36 that may be secured to or integrally formed with the body 29, and may permit the suture translation assembly 12 to extend through the guide member 36 and to translate relative to the guide member 36. In some cases, the body 29 may include an aperture 27 that may enable other devices to be inserted through the aperture 27. In some instances, as will be discussed with respect to subsequent Figures, the aperture 27 may be configured to accommodate a side-saddled lumen attachment element. In some cases, the aperture 27 may include one or more of a pin aperture 31a and a pin aperture 31b that may, for example, be used to mount the aforementioned side-saddled lumen attachment element, or possibly other features as well.

Figure 2:
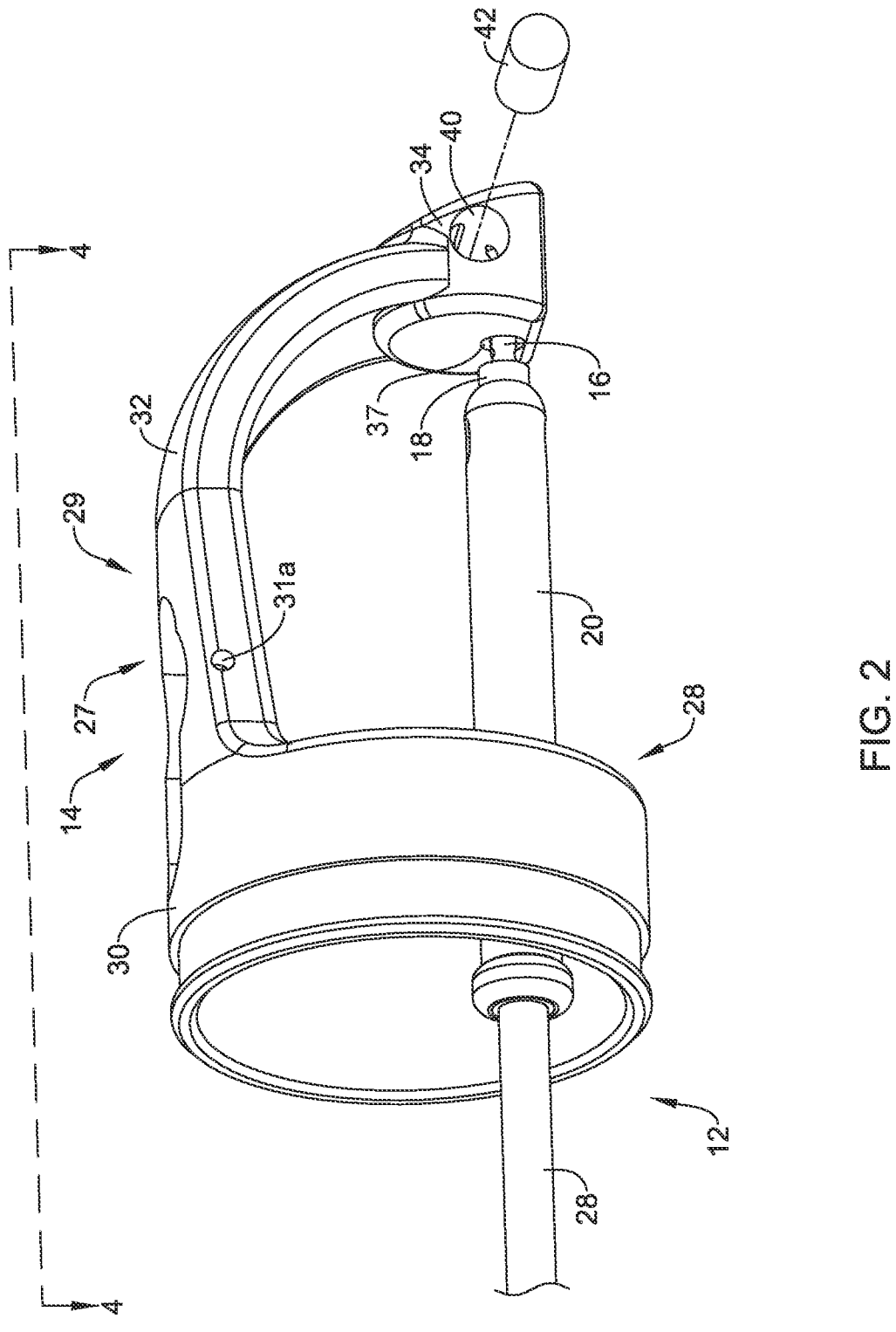
FIG. 2 is a perspective view of a distal assembly forming part of the illustrative suture device of FIG. 1, shown in an extended position.
Figure 3:
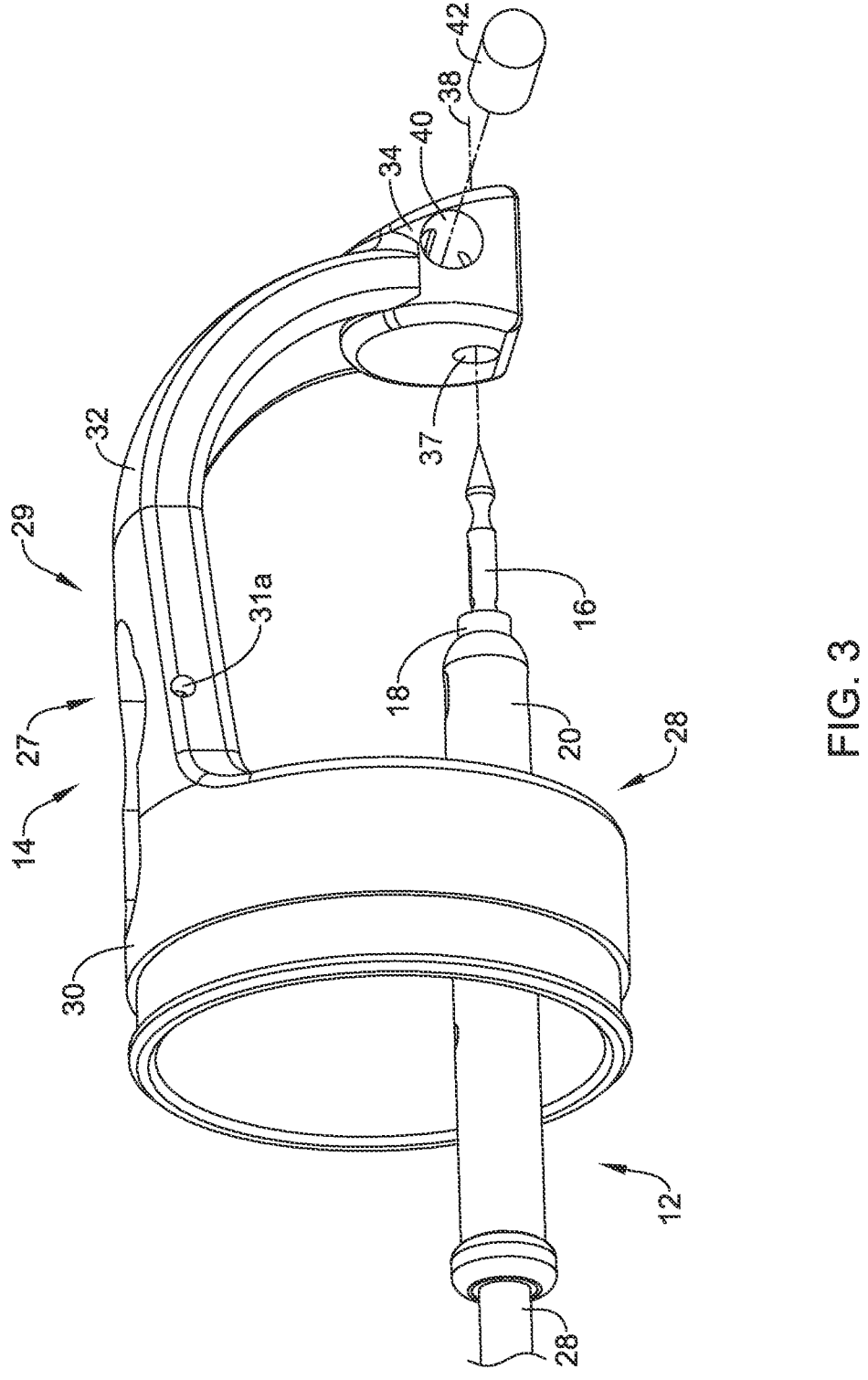
FIG. 3 is a perspective view of the distal assembly of FIG. 2, shown in a retracted position.

FIG. 2 and FIG. 3 show the suture translation assembly 12 extended through the guide member 36 and into the distal assembly 14. In FIG. 2, the suture translation assembly 12 is shown in an extended position in which the needle 16 extends into the endcap 34 while in FIG. 3, the suture translation assembly 12 is shown in a retracted position in which the needle 16 has been withdrawn proximally from the endcap 34. In some cases, as can be seen, the endcap 34 includes a proximal needle opening 37 that is configured to help guide the needle 16 into the proximal needle opening 37 as well as to accommodate the needle 16 when the needle 16 is advanced distally into the endcap 34. In some cases, the proximal needle opening 37 may extend all the way through the endcap 34 while in other cases the proximal needle opening 37 may not pass all the way through the endcap 34. In some instances, as shown, the proximal needle opening 37 may be considered as being aligned with a longitudinal axis 38 of the needle 16 (as shown in FIG. 3).

One or more securement openings 40 may be arranged orthogonal to the proximal needle opening 37 and one or more securements 42 that are configured to be disposed within the one or more securement openings 40, and which are configured to releasably engage the distal detent (as will be discussed) of the needle 16. In some cases, there may be a pair of securement openings 40, one on either side of the endcap 34. In some cases, there may be a pair of securements 42, with one disposed within each of the pair of securement openings 40. In some cases, while shown schematically, the one or more securements 42 may be springs or coils, for example.

Figure 4:
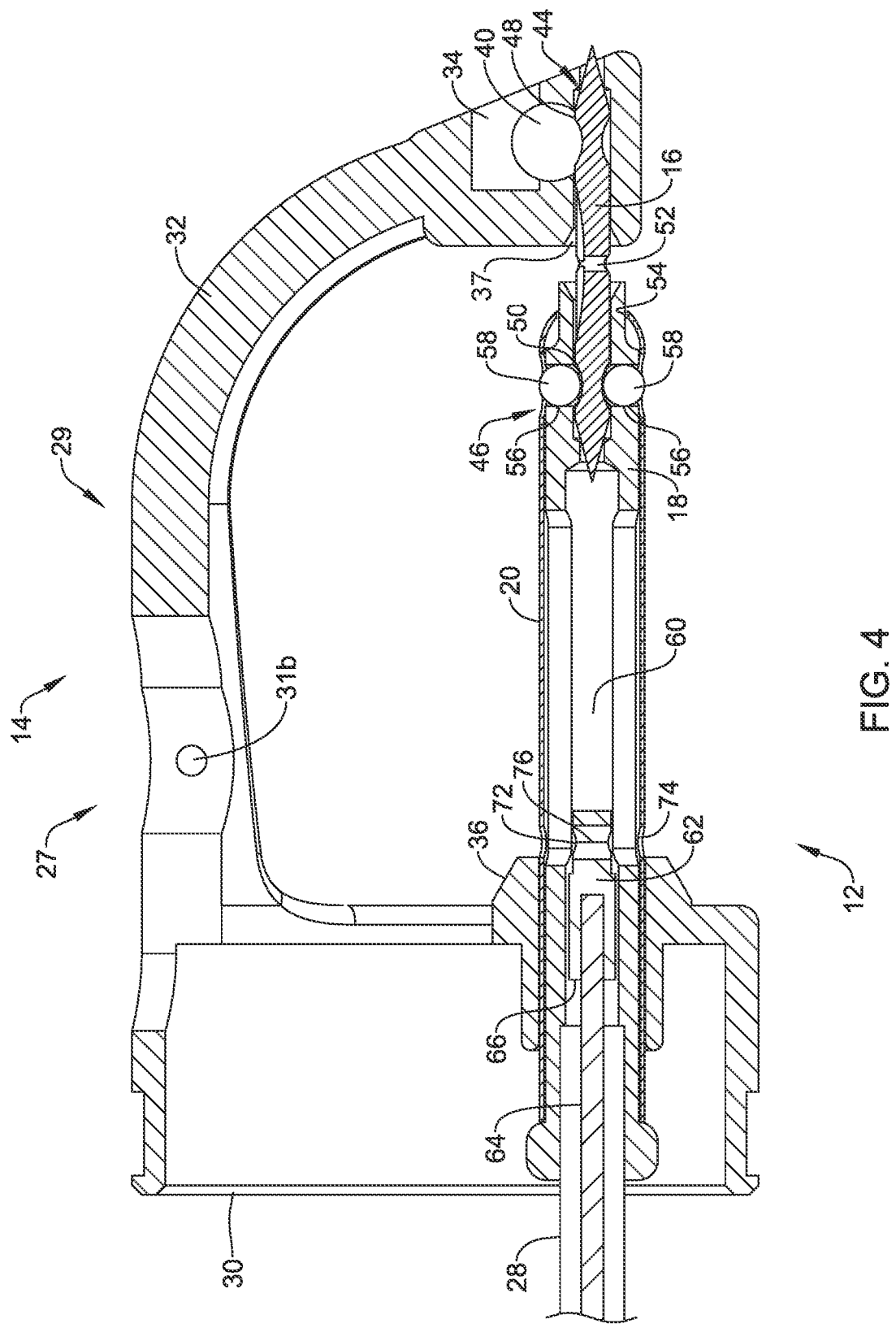
FIG. 4 is a cross-sectional view of the distal assembly of FIG. 2, taken along the line 4-4.
Figure 5:
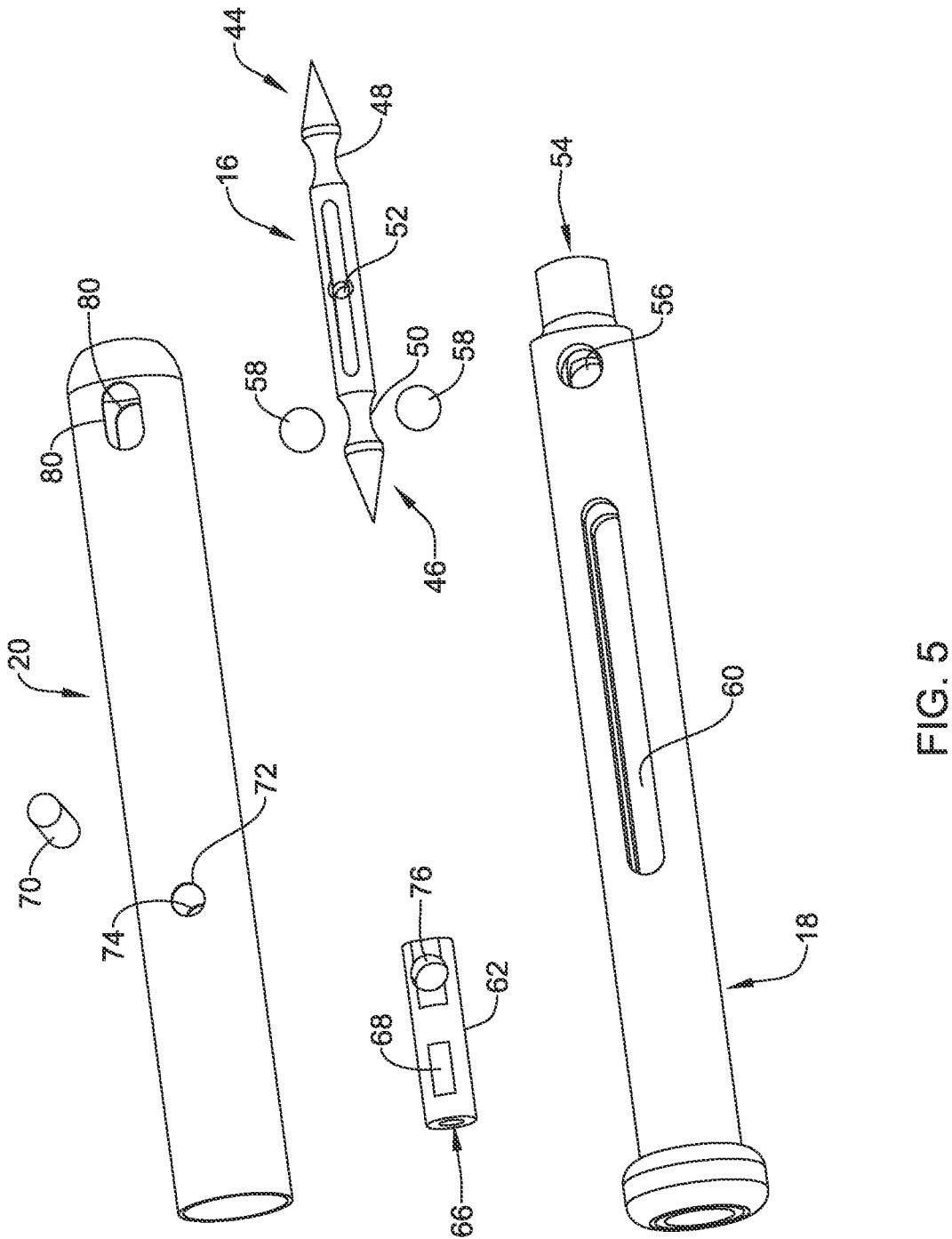
FIG. 5 is an exploded view of a portion of a suture translation assembly forming part of the illustrative suture device of FIG. 1.

FIG. 4 is a cross-sectional view of the distal assembly 14, with the suture translation assembly 12 disposed within the distal assembly 14. FIG. 5 is an exploded view of the suture translation assembly 12. The needle 16 may be considered as including a distal region 44 and a proximal region 46. In some cases, the distal region 44 may include a distal detent 48 for releasably engaging the endcap 34 and the proximal region 46 may include a proximal detent 50 for releasably engaging the distal shuttle 18. The needle 16 may, as shown, include an aperture 52 for accommodating a suture line passing therethrough.

In some cases, the distal shuttle 18 may be considered as including a distal needle opening 54 that is configured to accommodate the needle 16 when the distal shuttle 18 is advanced distally over the needle 16 and that is aligned with the longitudinal axis 38 of the needle 16. One or more bearing ball openings 56 may be arranged orthogonal to the distal needle opening 54 such that the one or more bearing ball openings 56 align with the proximal detent 50 when the needle 16 is secured to the distal shuttle 18. In some cases, one or more bearing balls 58 may be disposed within the one or more bearing ball openings 56 and may be configured to be disposed within the proximal detent 50 when the needle is secured to the distal shuttle 18.

In some cases, the distal shuttle 18 includes an internal void 60 and a sleeve capture member 62 that is slidingly disposed within the internal void 60. In some cases, the sleeve capture member 62 may be coupled to a cable 64 extending distally from the user interface 22 within the shaft 28 and into a cable aperture 66 and secured via a crimp or other mechanical connection 68. In some cases, the sleeve capture member 62 may be coupled to the sleeve 20 via a pin 70 that extends through first and second sleeve connection apertures 72, 74 and a corresponding aperture 76 extending through the sleeve capture member 62 as well as extending through the internal void 60. As the cable 64 is operably coupled to the translating handle 26 (as will be discussed), it will be appreciated that moving the translating handle 26 distally or proximally relative to the proximal handle 24 causes a corresponding distal or proximal movement of the sleeve 20 relative to the distal shuttle 18.

In some cases, the sleeve 20 includes one or more sleeve openings 80 that may be smaller in diameter, or smaller in width, than the diameter of the one or more bearing balls 58. In some cases, the sleeve 20 may include a pair of sleeve openings 80, corresponding to a pair of bearing ball openings 56 and a pair of bearing balls 58. When the sleeve 20 is in the locked position, as shown for example in FIG. 6A, the one or more sleeve openings 80 are misaligned with, or do not align with, the one or more bearing ball openings 56, and so the one or more bearing balls 58 engage the proximal detent 50 of the needle 16. The sleeve 20 prevents the one or more bearing balls 58 from being pushed out of the proximal detent 50.

Figure 6A:
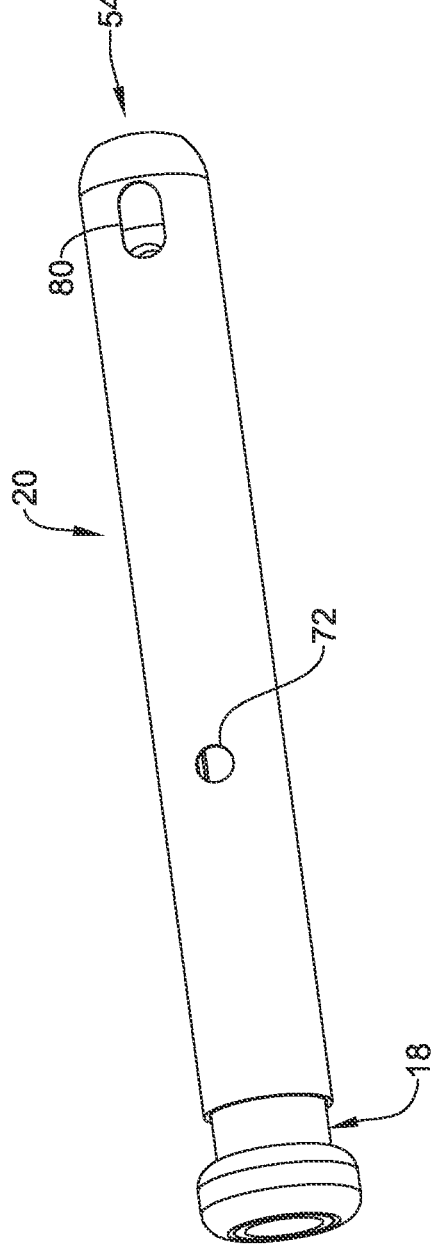
FIG. 6A is a side view of a distal shuttle and a member forming part of the suture translation assembly, with the member shown extended in a locked position.
Figure 6B:
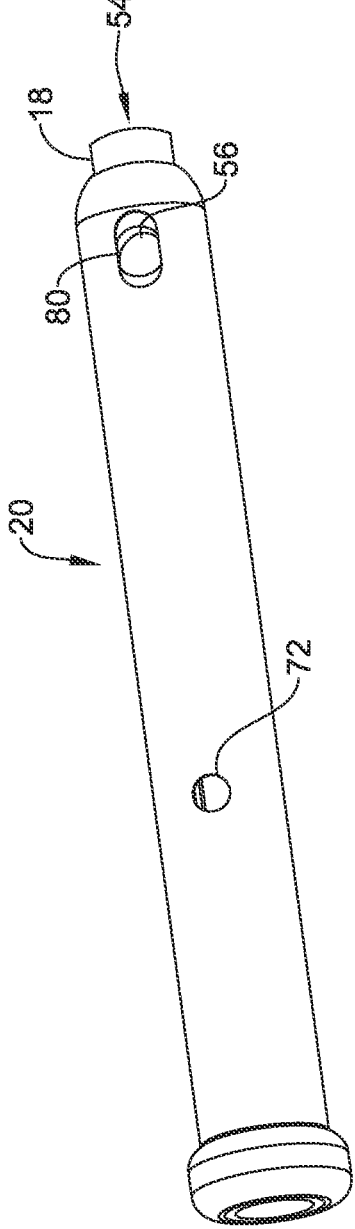
FIG. 6B is a side view of the distal shuttle and the member of FIG. 6A, with the member shown retracted in an unlocked position.

Conversely, when the sleeve 20 is in the unlocked position, as shown for example in FIG. 6B, the one or more sleeve openings 80 are aligned with the one or more bearing ball openings 56. This permits the one or more bearing balls 58 to move radially out, into the one or more sleeve openings 80, a distance sufficient to permit the one or more bearing balls 58 to clear the proximal detent 50 of the needle 16 in response to a force applied to the one or more bearing balls 58 by the needle 16. With reference to FIG. 4, while the suture translation assembly 12 is shown advanced into the distal assembly 14, the sleeve 20 is in the unlocked position relative to the distal shuttle 18, and thus the one or more bearing balls 58 may be seen as extending partially into the one or more sleeve openings 80.

In some cases, it will be appreciated that the distal shuttle 18, and the sleeve 20, in combination, provide an active connection to the needle 16 while the distal endcap 34 provides a passive connection to the needle 16. If the needle 16 is moved distally into the distal endcap 34, the distal endcap 34 will grab onto the needle 16, with the one or more securements 42 engaging the distal detent 48. If the needle 16 is subsequently moved proximally, the axial force applied overcomes any resistance provided by the one or more securements 42, and the needle 16 is able to move proximally. In contrast, the active connection to the needle 16 provided by the distal shuttle 18 and the sleeve 20, however, requires action to move the sleeve 20, relative to the distal shuttle 18, between the locked position and the unlocked position. The user interface 22 provides a mechanism for positively moving the sleeve 20 between the locked and unlocked positions.

Figure 7:
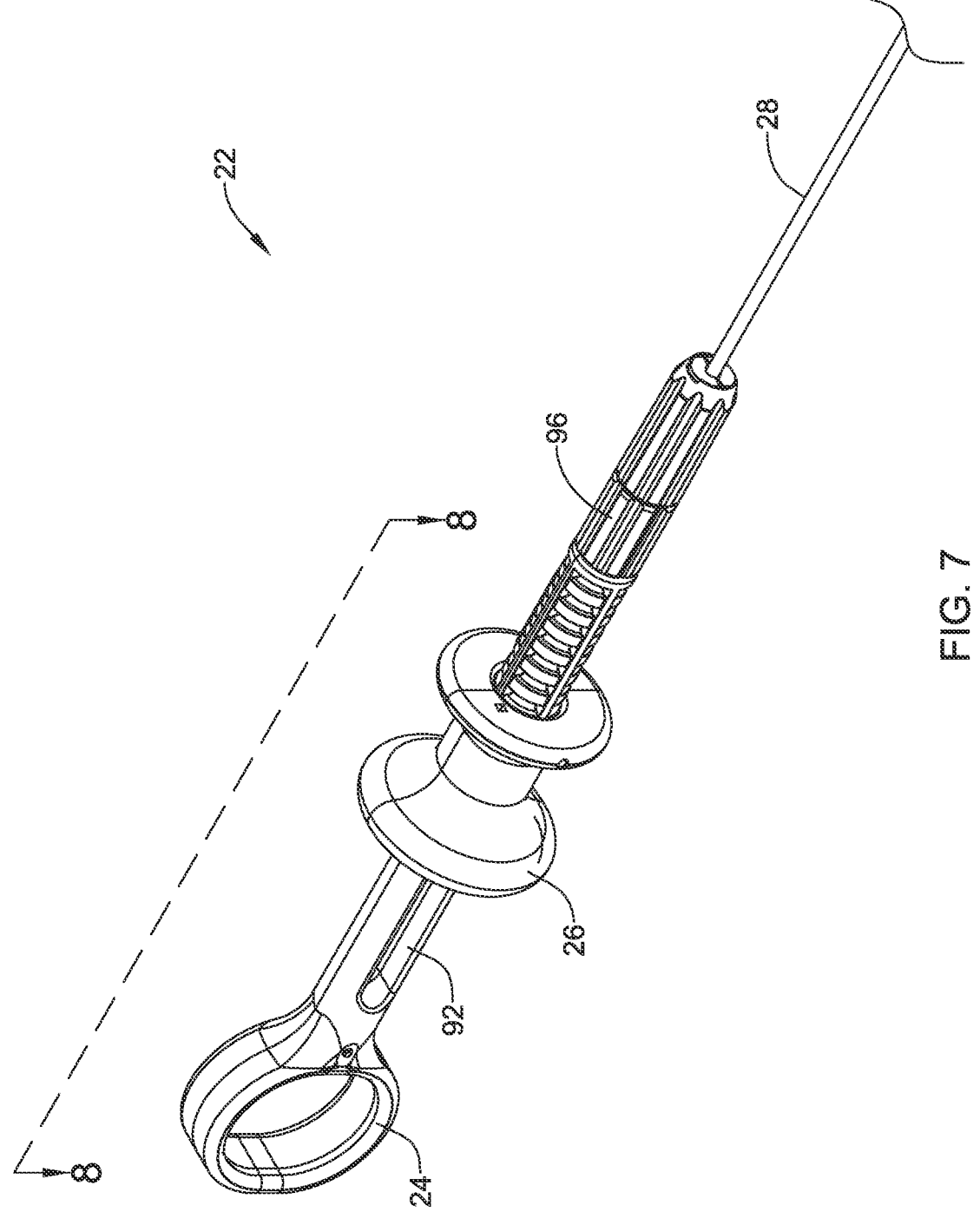
FIG. 7 is a perspective view of a handle portion of a suture translation assembly forming part of the illustrative suture device of FIG. 1.
Figure 8:
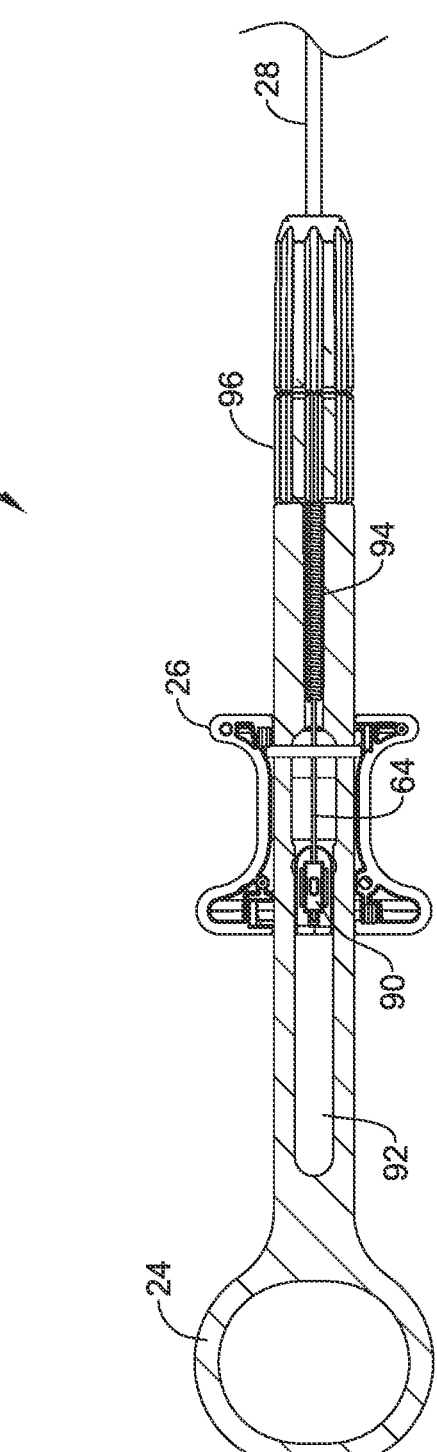
FIG. 8 is a cross-sectional view of the handle portion of FIG. 7, taken along the line 8-8.

FIG. 7 is a perspective view of the user interface 22 and FIG. 8 is a cross-sectional view along line 8-8 of FIG. 7. The cable 64, which extends through the shaft 28, is coupled to the translating handle 26 via a connector 90. The connector 90 is able to translate relative to the proximal handle 24, and thus enable the translating handle 26 to translate relative to the proximal handle 24, by translating within a void 92 formed within the proximal handle 24. In some cases, the shaft 28 includes a coil 94. It will be appreciated that the relative position of the translating handle 26 (relative to the proximal handle 24) shown in FIGS. 7 and 8 corresponds to the sleeve 20 being in the locked position (as shown in FIG. 6A). In some cases, the proximal handle 24 includes a handle portion 96.

Figure 9A:
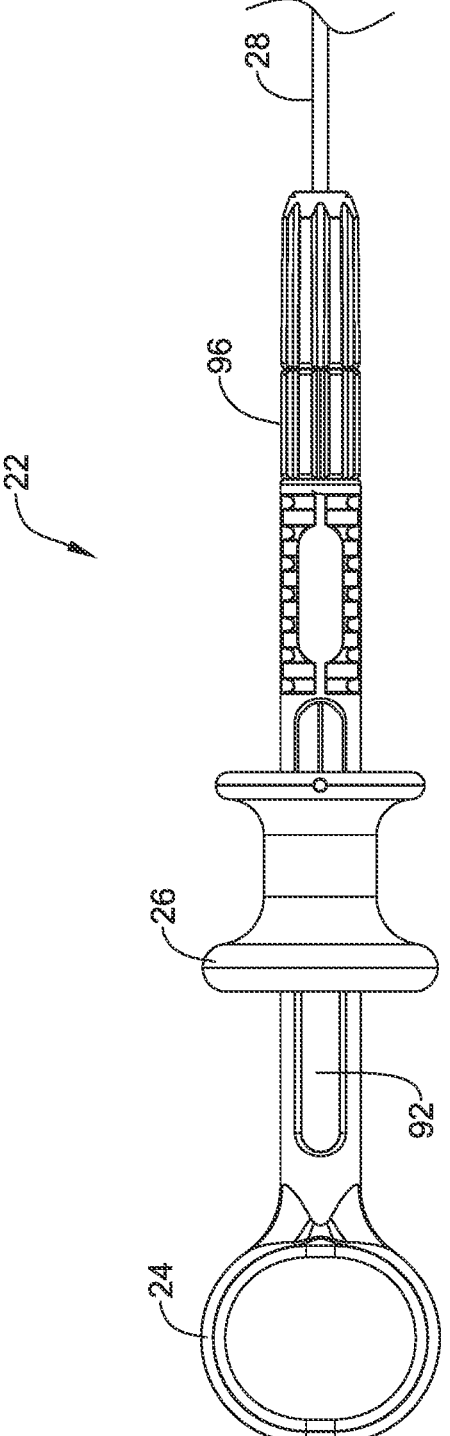
FIG. 9A is a perspective view of the handle portion of FIG. 7, shown in an intermediate position.
Figure 9B:
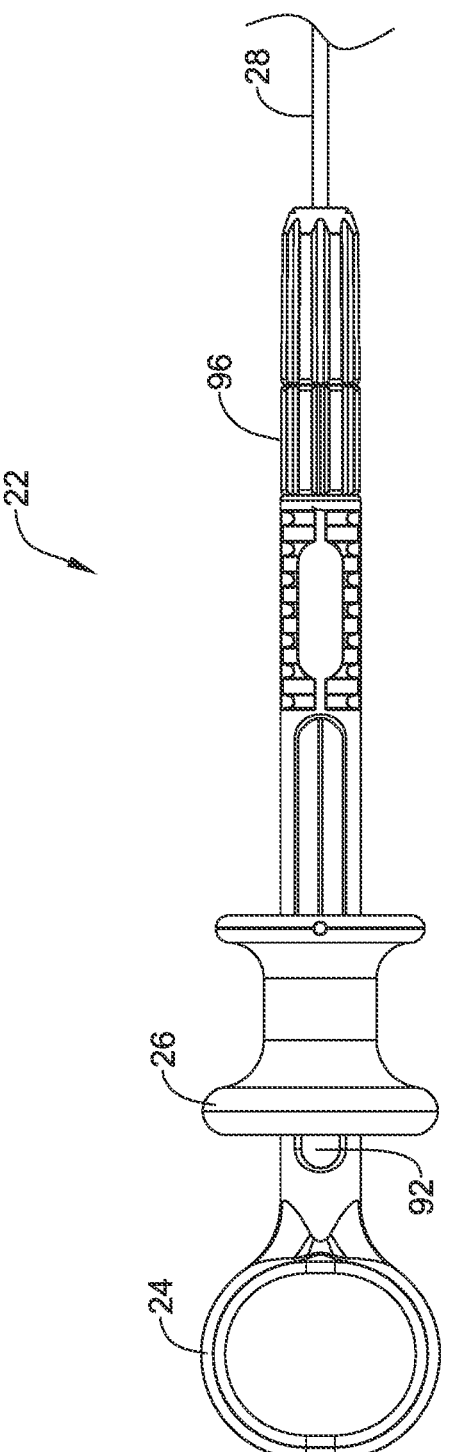
FIG. 9B is a perspective view of the handle portion of FIG. 8, shown in a retracted, unlocked position.

FIG. 9A is a perspective view of the user interface 22 with the translating handle 26 shown in an intermediate position relative to the proximal handle 24 while FIG. 9B is a perspective view of the user interface 22 with the translating handle 26 shown in a retracted, unlocked position. Accordingly, to move the sleeve 20 into the locked position, a user may move the translating handle 26 distally relative to the proximal handle 24, from the neutral position. To move the sleeve 20 into the unlocked position, a user may move the translating handle 26 proximally relative to the proximal handle 24, from the neutral position. In some cases, a user has to intentionally engage the translating handle 26 in order to lock or unlock the needle 16 relative to the distal shuttle 18.

Figure 10:
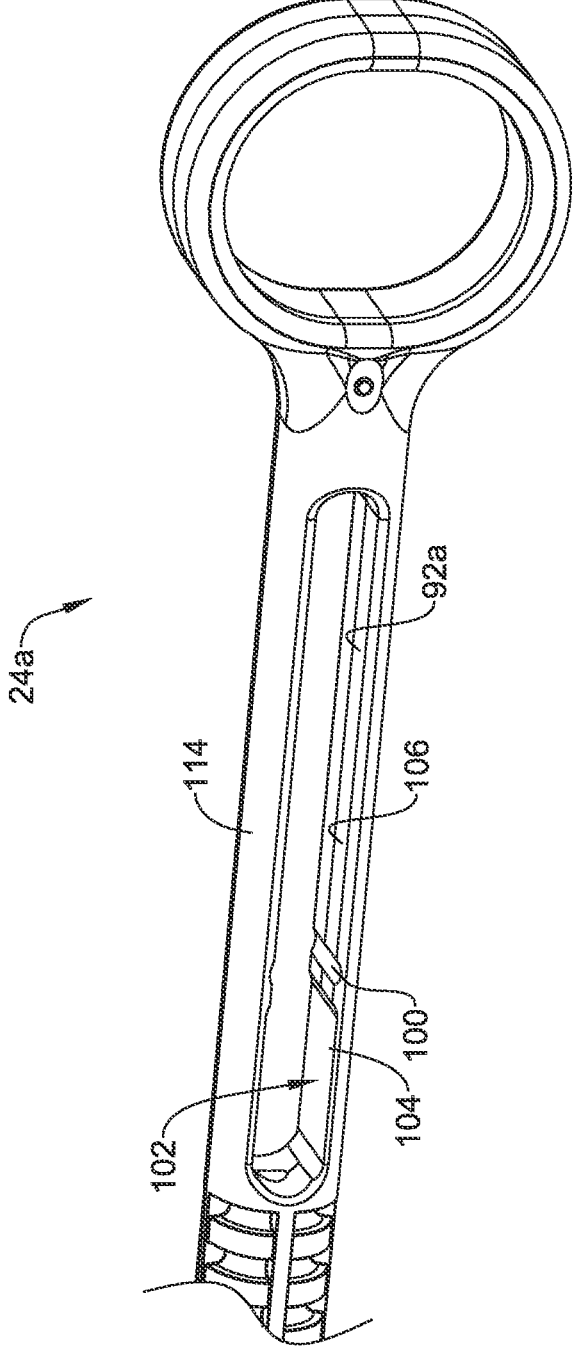
FIG. 10 is a perspective view of a proximal handle in accordance with an example of the disclosure.

FIG. 10 is a side view of an alternate proximal handle 24a that may, for example, be used in forming the user interface 22. In some cases, the proximal handle 24a may include a void 92a having several one or more handle detents 100 that are formed within a surface 102 of the void 92a. In some cases, the surface 102 may include one or more distinct sections 104, 106 that provide varying frictional forces to a friction disk that may be secured within the translating handle 26 and that may interact with the surface 102 as the translating handle 26 is moved distally and proximally relative to the proximal handle 24*a*. In some cases, providing varying frictional forces to a friction disk can provide feedback to an operator as to the position of the translating handle 26 relative to the proximal handle 24*a*, and thus provide the operator with feedback as to whether the sleeve 20 (FIG. 1) is in locked position, an unlocked position or an intermediate position.

Figure 11B:
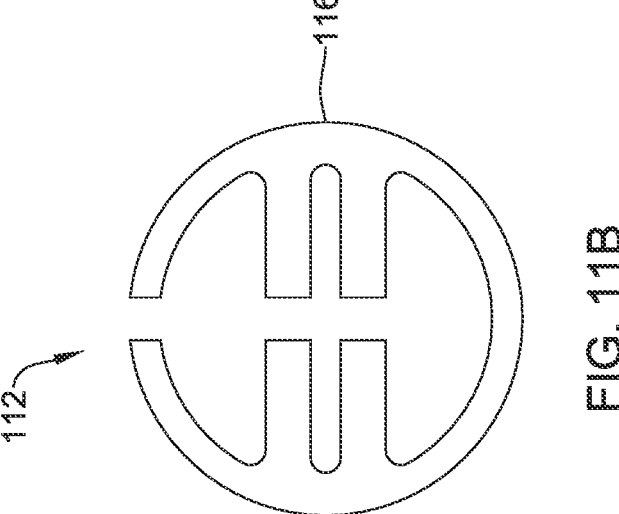
FIGS. 11A and 11B are front views of friction disks usable with the proximal handle of FIG. 10.
Figure 11A:
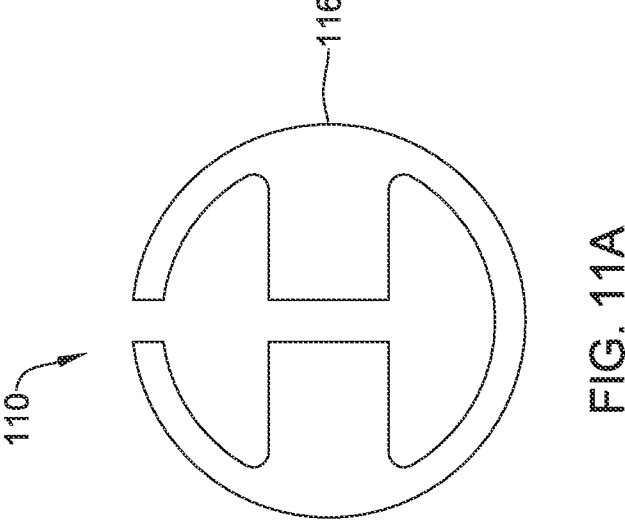
Figure 12:
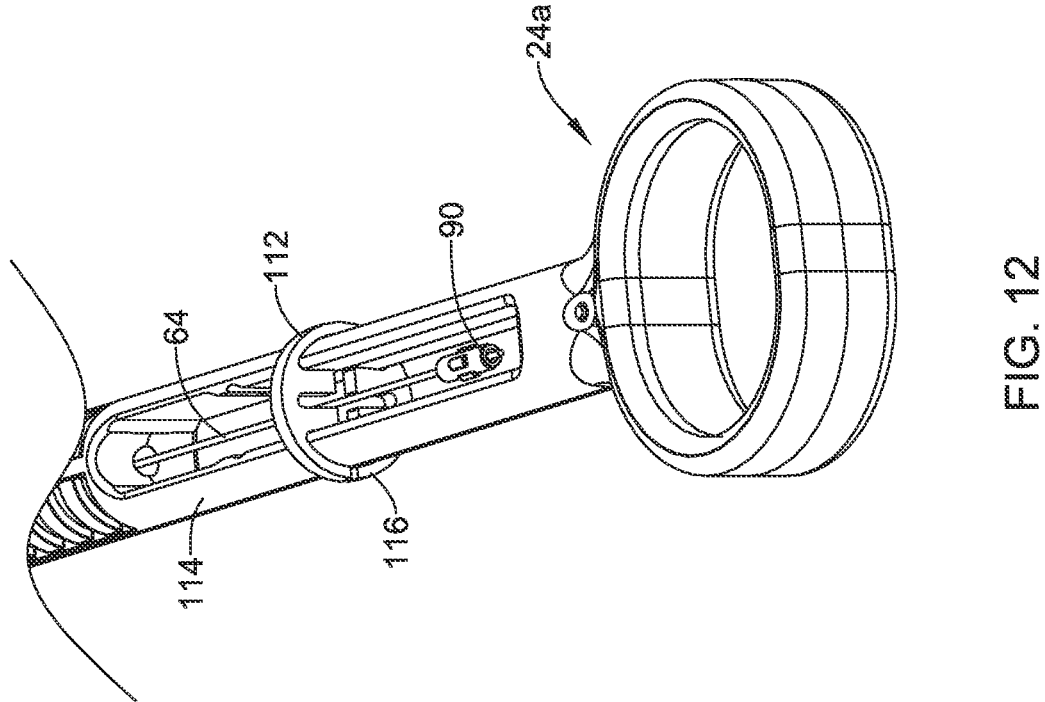
FIG. 12 is a perspective view of the proximal handle of FIG. 10 in combination with the friction disk of FIG. 11B.
Figure 13:
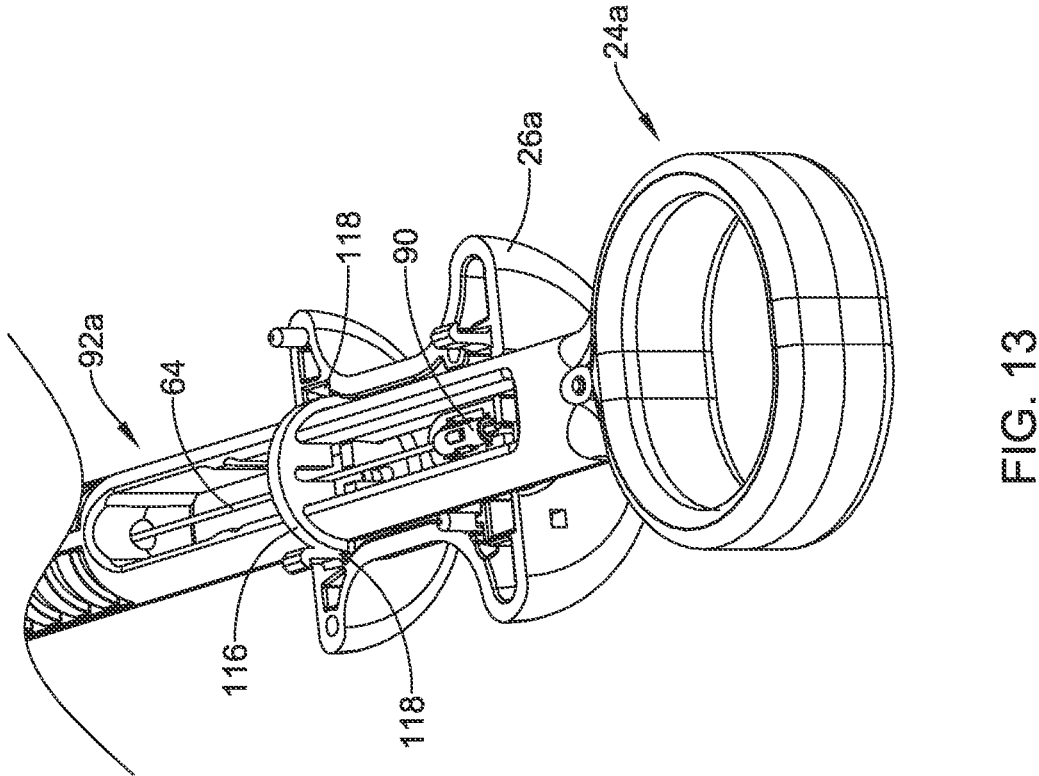
FIG. 13 is a partial cross-sectional perspective view of the assembly of FIG. 12 in combination with a translating handle in accordance with an example of the disclosure.

FIGS. 11A and 11B provide illustrative but non-limiting examples of friction disks that may be used. In FIG. 11A, a friction disk 110 may be seen as having a circular outer profile 116 and one or more voids or slots configured to accommodate features on the proximal handle 24*a*. Similarly, in FIG. 11B, a friction disk 112 may be seen as having a circular outer profile 116 and one or more voids or slots configured to accommodate features on the proximal handle 24*a*. The friction disks 110, 112 may be formed of any suitable material such as Delrin and may be dimensioned to slidingly engage an outer surface 114 of the proximal handle 24*a*. FIG. 12 shows the friction disk 112 disposed about the proximal handle 24*a* while FIG. 13 also shows a translating handle 26*a* in position relative to the proximal handle 24*a*. As can be seen for example in FIG. 13, the outer profile 116 of the friction disk 112 engages into a corresponding slot 118 formed within the translating handle 26*a* such that as the translating handle 26*a* moves distally or proximally relative to the proximal handle 24*a*, the friction disk 112 frictionally engages the outer surface 114 of the proximal handle 24*a*.

Figure 14:
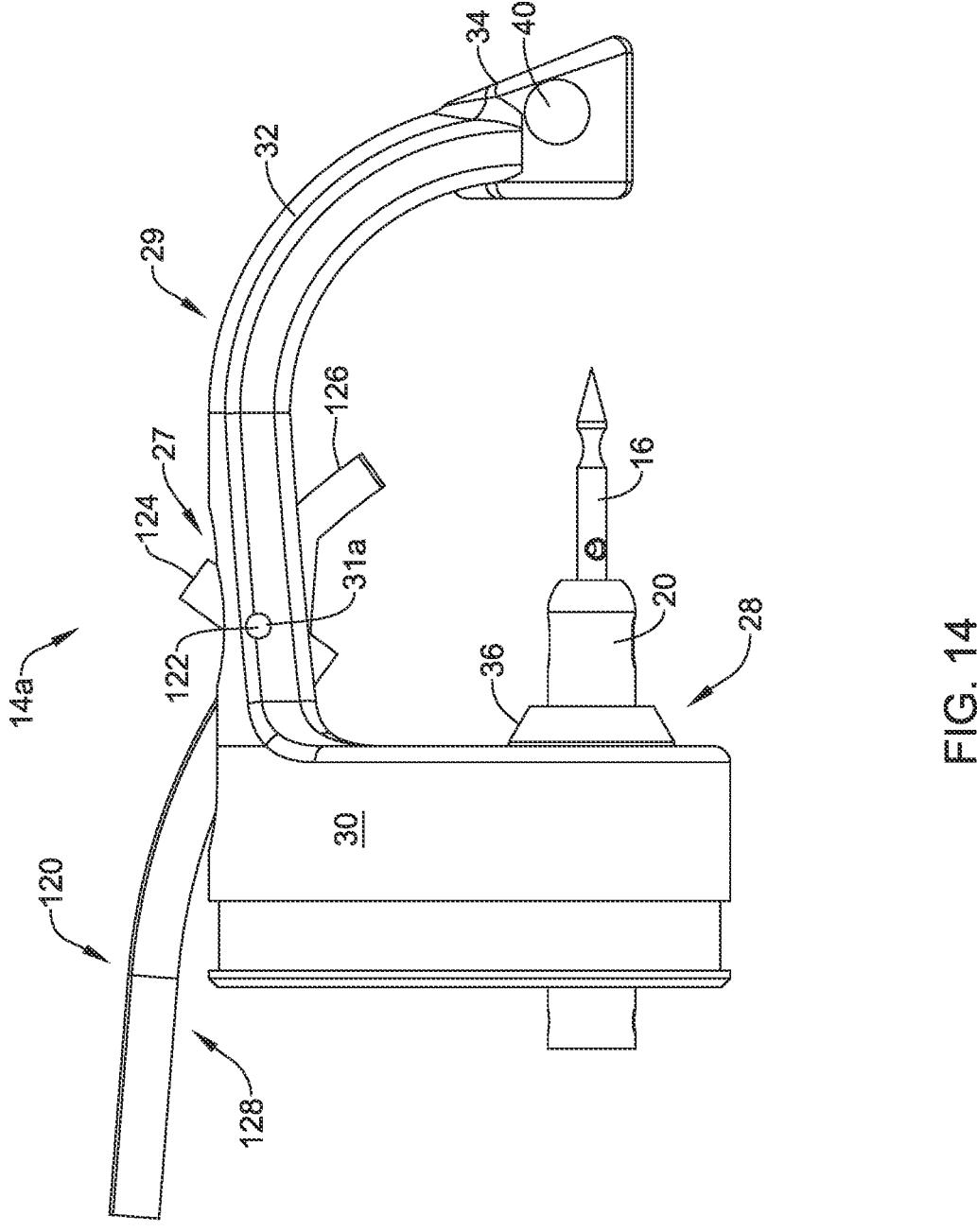
FIG. 14 is a side view of a distal assembly usable in the suture device of FIG. 1 in accordance with an example of the disclosure.

FIG. 14 is a side view of a distal assembly 14*a* that may, for example, be usable in the suture device 10 shown in FIG. 1. The distal assembly 14*a* is similar to the distal assembly 14 shown in previous Figures, but includes a side-saddled lumen attachment element 120 that is coupled to the body 29 of the distal assembly 14*a*. In some cases, the side-saddled lumen attachment element 120 may include one or two pegs 122 that fit into the pin apertures 31*a* and 31*b* (pin aperture 31*a* is visible in this view) and thus enable the side-saddled lumen attachment element 120 to pivot relative to the body 29 of the distal assembly 14*a*. In some cases, the side-saddled lumen attachment element 120 includes a ring 124, from which the pegs 122 extend, a distal region 126 and a body 128 that in some instances has a curvature to it.

Figure 15:
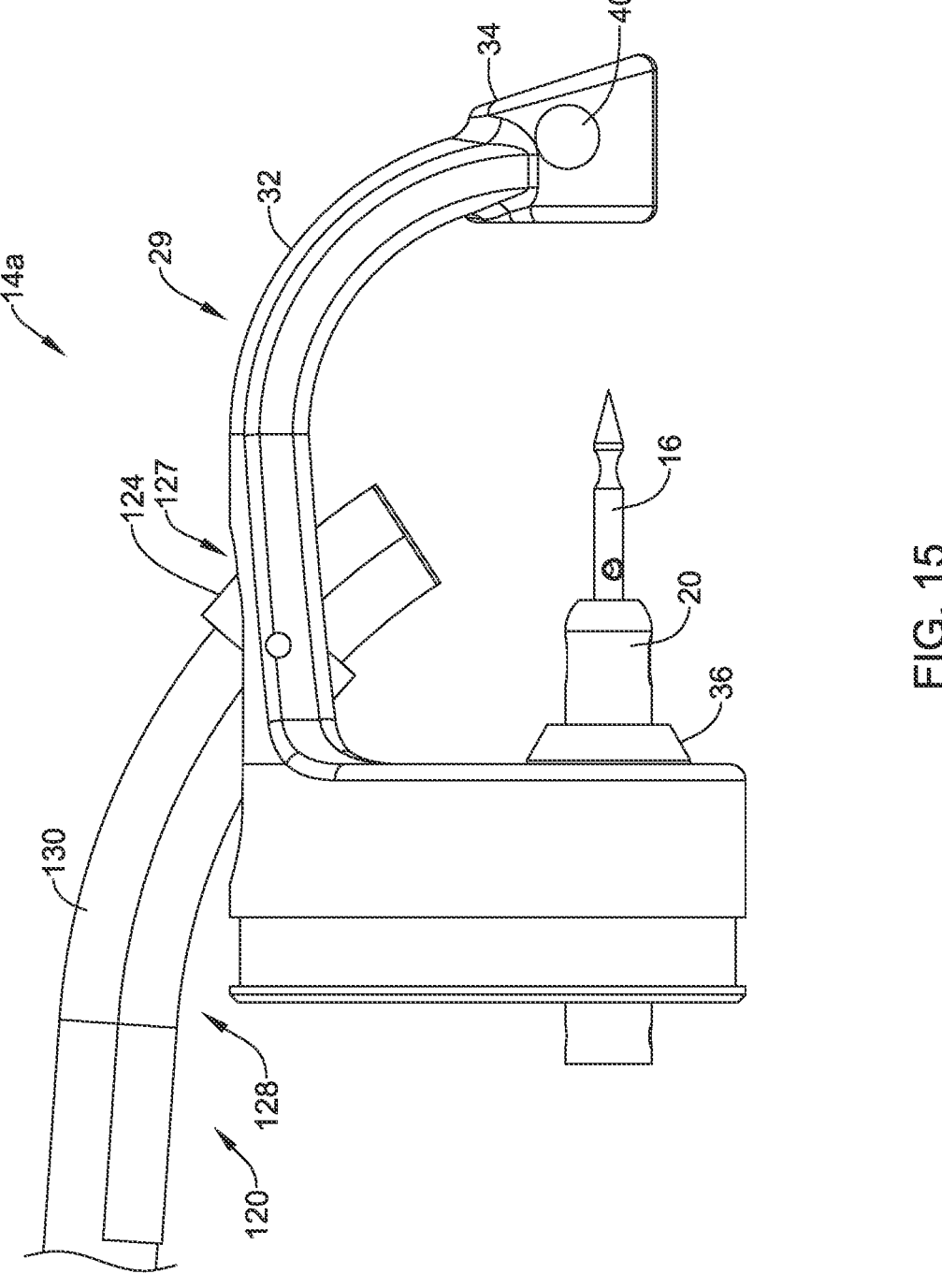
FIG. 15 is a side view of the distal assembly of FIG. 14 in combination with an attached flexible lumen.

In some cases, the distal region 126 and the body 128 have a semi-circular profile in order to accommodate a lumen such as a flexible lumen 130 that may engage within the side-saddled lumen attachment element 120 via a frictional or compressive fit as shown in FIG. 15. The flexible lumen 130 may be polymeric or metallic. A polymeric lumen may, for example, be expanded to a full working dimension by extending a mandrel through the flexible lumen 130 after the flexible lumen 130 has been placed relative to the side-saddled lumen attachment element 120.

In some cases, the side-saddled attachment element 120 (and accompanying flexible lumen 130) may be used as a secondary working channel and may contain the suture used in the procedure. In some cases, it may be large enough to accommodate secondary tools for use during the procedure for tissue acquisition or manipulation allowing secondary tool use without requiring a dedicated dual-channel delivery system such as a dual channel endoscope. If desired, a dual-channel delivery system could be used to provide even more options in a procedure. The side-saddled attachment element 120 may have an exit port in the distal assembly 14*a* such that secondary tools extend along an axis suitable for tissue manipulation. This axis may cross the axis of the suture carrying element, allowing a secondary tool to pull tissue into the suture carrying element's projected path. For example, this could be used to pull tissue in line with a needle to assist in driving the needle 16 through the tissue. Maintaining tension on the suture through the side-saddled attachment element 120 may keep the suture from interfering with the procedure.

Figure 16:
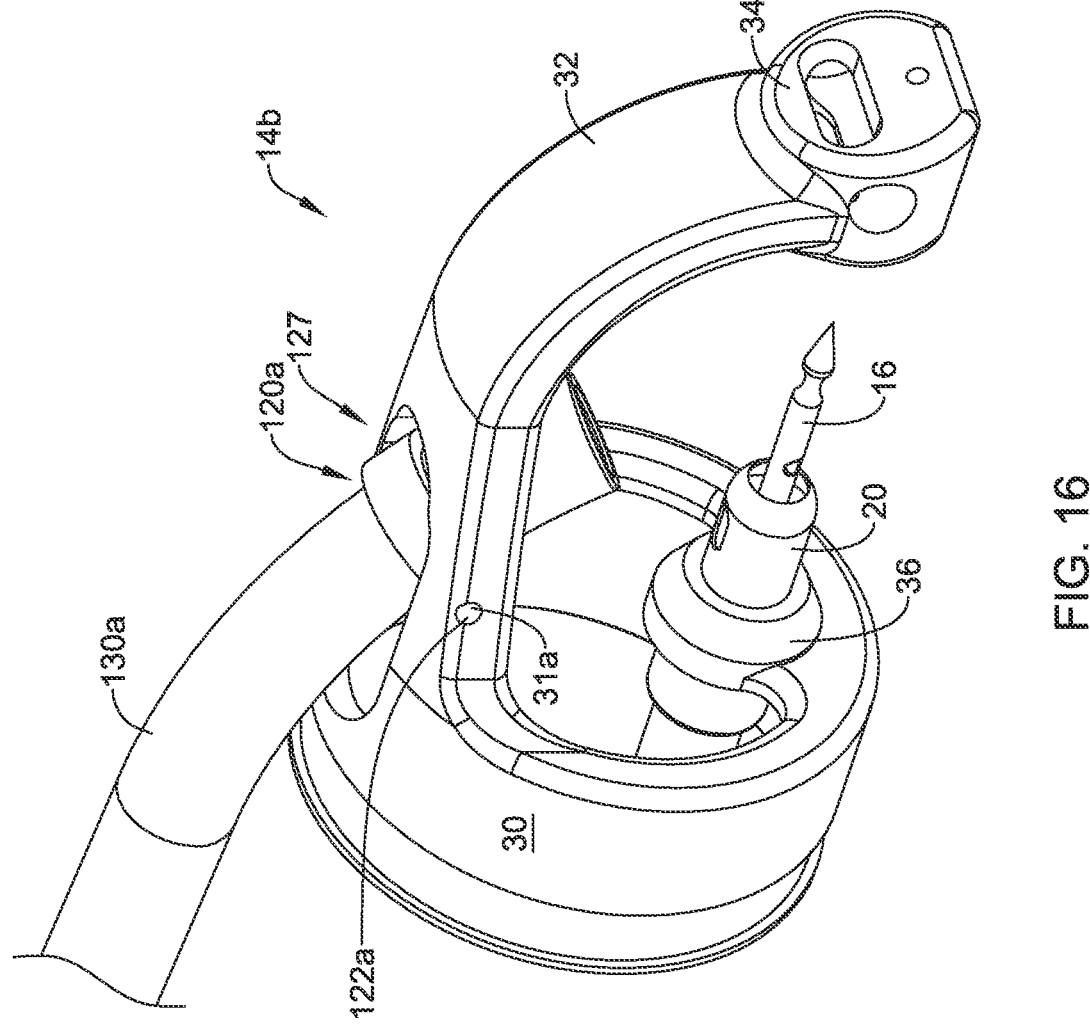
FIG. 16 is a side view of a distal assembly usable in the suture device of FIG. 1, shown with an attached lumen, in accordance with an example of the disclosure.

FIG. 16 is a perspective view of a distal assembly 14*b* that includes a shorter side-saddled lumen attachment element 120*a* that may be pivotally secured to the body 29 via one or more pegs 122*a* that extend into the pin apertures 31*a*, 31*b*. A lumen 130*a* coupled with the side-saddled lumen attachment element 120*a* to provide a working channel through which the suture or other tools may be extended.

Figure 17B:
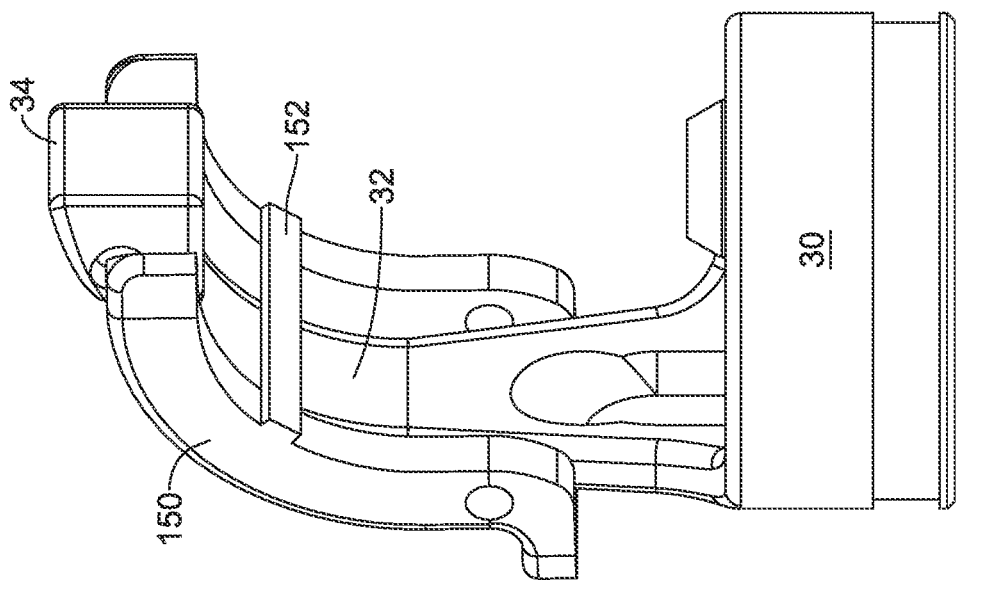
FIGS. 17A and 17B are views of a tissue release mechanism that may be used in combination with the distal assemblies of FIGS. 1 and 14 in accordance with an example of the disclosure.
Figure 17A:
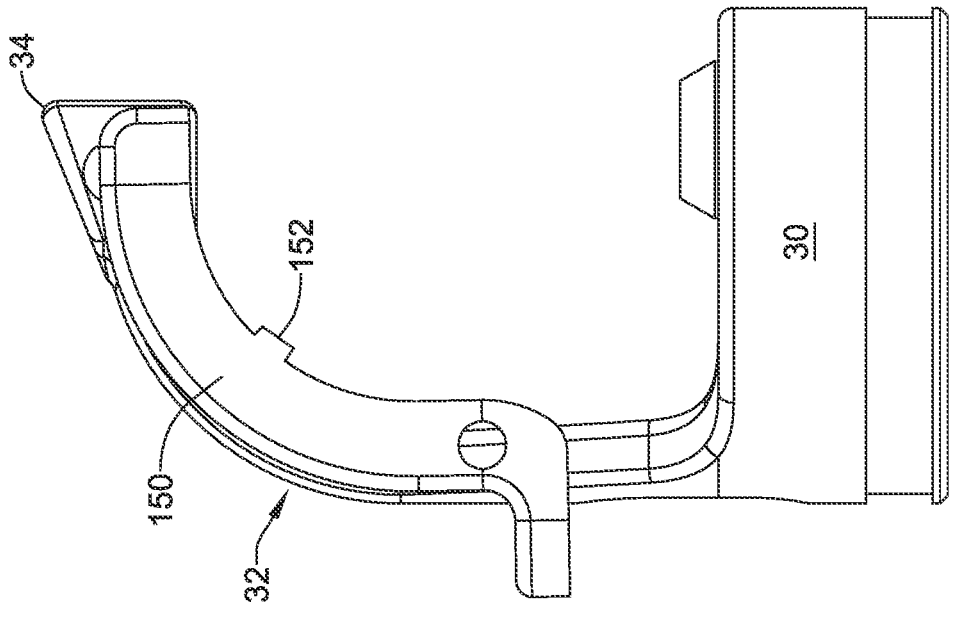

FIGS. 17A and 17B are views of a tissue release mechanism 150 that may fit over the arm 32. In some cases, the tissue release mechanism 150 may assist in a procedure by helping to remove tissue that may otherwise become stuck on the needle 16. In some instances, the tissue release mechanism 150 may be spring-loaded to engage the needle 16, or may be separately and independently actuated. In some instances, the tissue release mechanism 150 includes a cross-bar 152 that provides an additional surface that can push tissue off of the needle 16.

In preparing the suture device 10 for use, the distal assembly 14 may be secured to a delivery device such as an endoscope. In some cases, an attachment enabler, such as a flexible silicone tube, may be unrolled along the delivery device in order to hold the distal assembly 14 in place and to prevent rotation of the distal assembly 14 relative to the delivery device. In some cases, if desired, the side-saddled lumen attachment element 120 (or 120*a*) may be secured to the distal assembly 14. The suture may be passed through the needle 16, and fed back towards the user interface 22. The device 10 may be extended through the body to the defect site. In some cases, the defect may require a full thickness repair, while in other cases, the defect may not pass through all of the tissue layers. FIGS. 18 through 25 provide an illustrative but non-limiting example of a full thickness tissue repair while FIGS. 26 through 32 provide an illustrative but non-limiting example of a partial thickness tissue repair.

Figure 18:
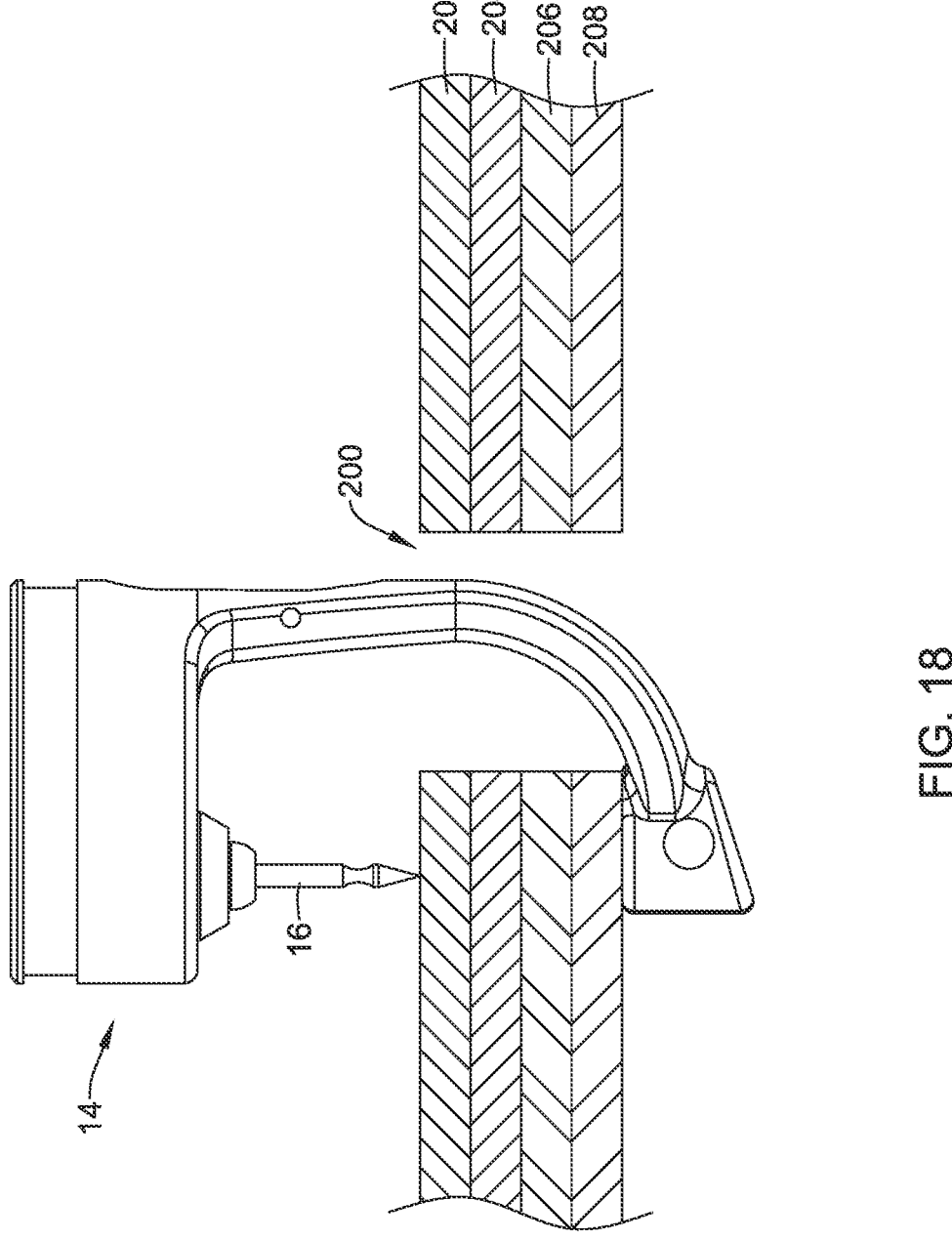
FIGS. 18 through 25 illustrate use of a suture device in a full thickness procedure in accordance with an example of the disclosure.
Figure 19:
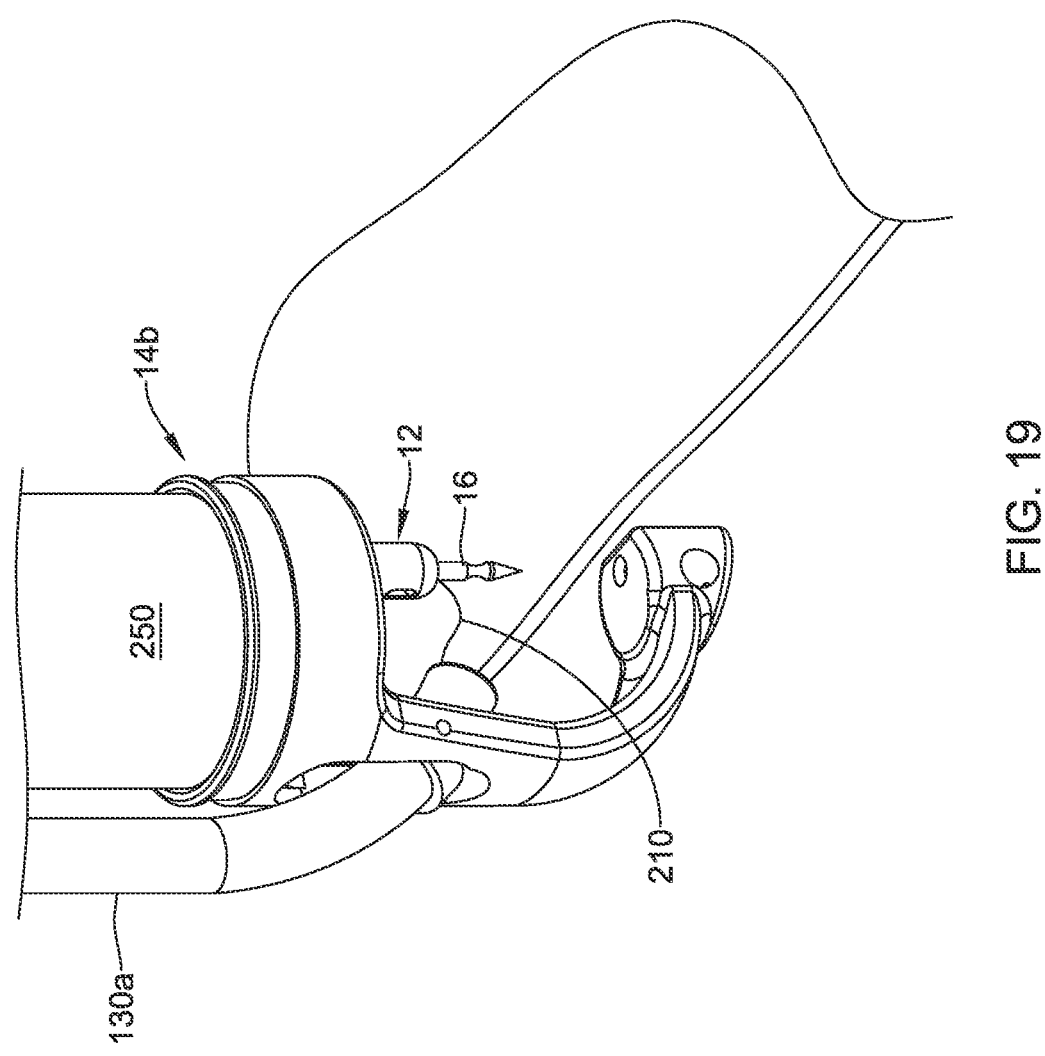
Figure 20:
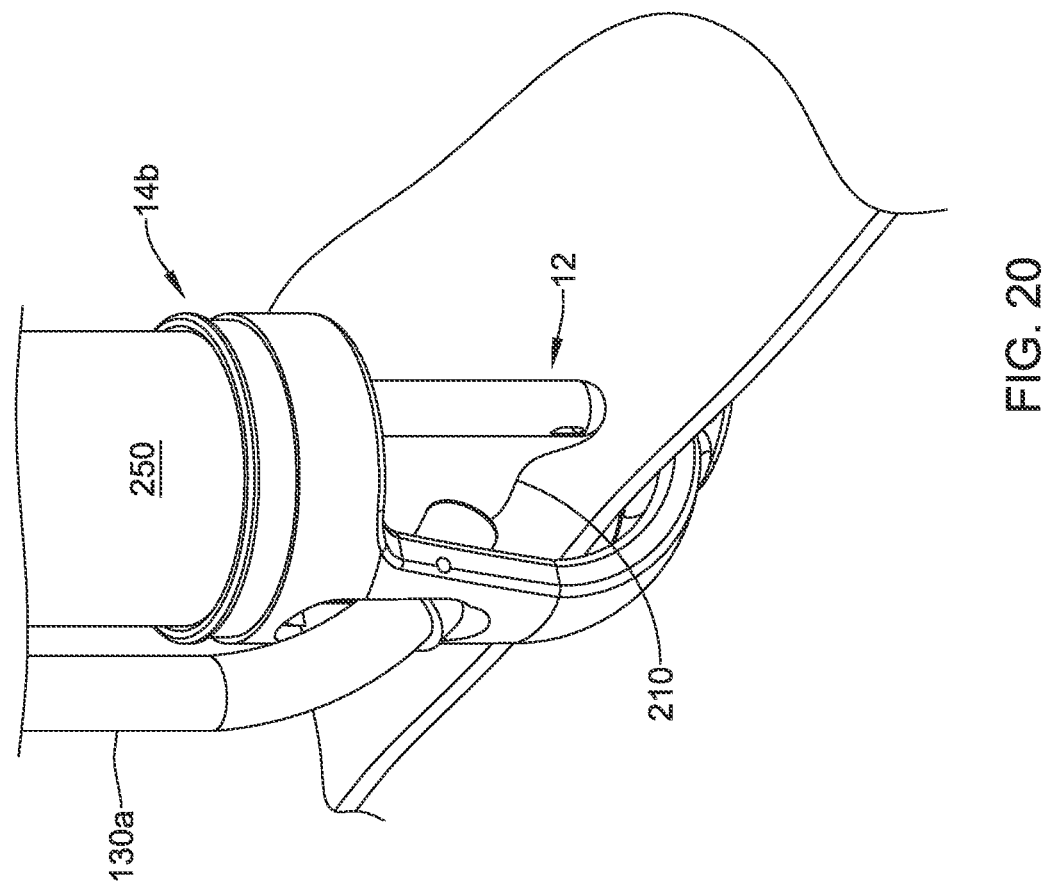
Figure 21:
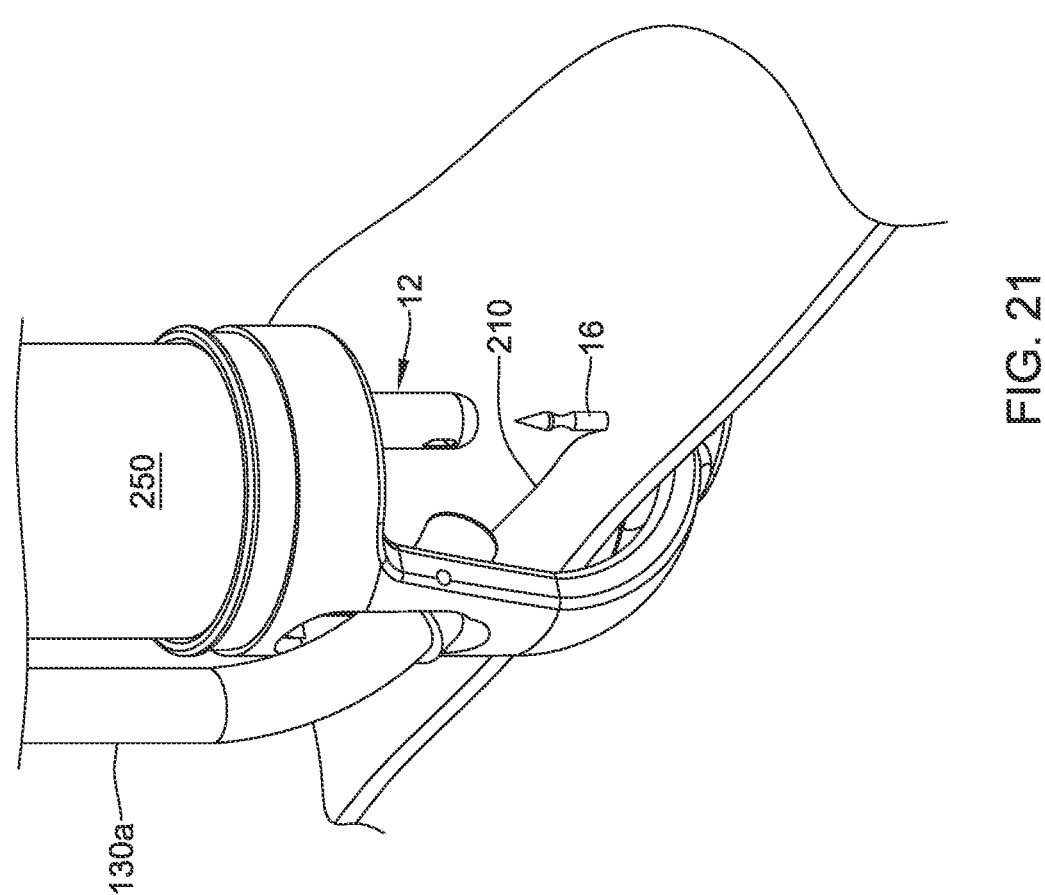

FIG. 18 shows the distal assembly 14 positioned relative to a defect 200. In this example, the defect 200 extends through the mucosa layer 202, the submucosa layer 204, the muscularis layer 206 and the serosa layer 208. Starting in FIG. 19, the distal assembly 14*b* is coupled to an endoscope 250, and has been positioned with a suture 210 coupled to the needle 16. The suture 210 may, for example, be monofilament, braided, barbed and the like. As seen in FIG. 20, the suture translation element 12 has been pushed distally until the needle 16 pushes through the tissue and locks into the endcap 34 (not visible). Next, and as shown in FIG. 21, with the needle 16 locked into the endcap 34, the user pulls on the translating handle 26 to unlock the needle 16 and pulls the suture device 10 proximally clear of the needle 16. The endoscope 250 may be pushed distally to pass the needle 16 entirely through the tissue. This completes the first suture site.

Figure 22:
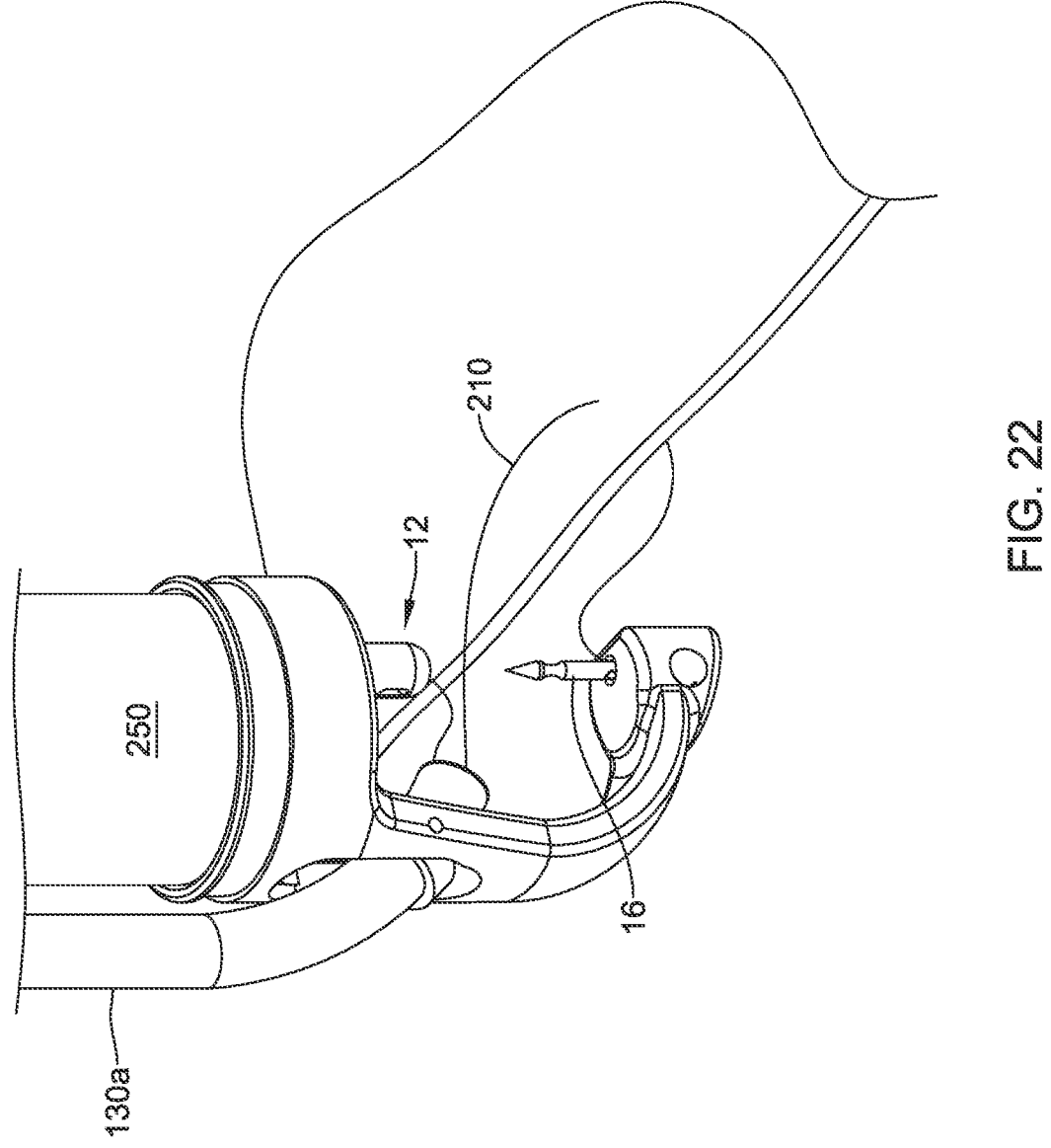
Figure 23:
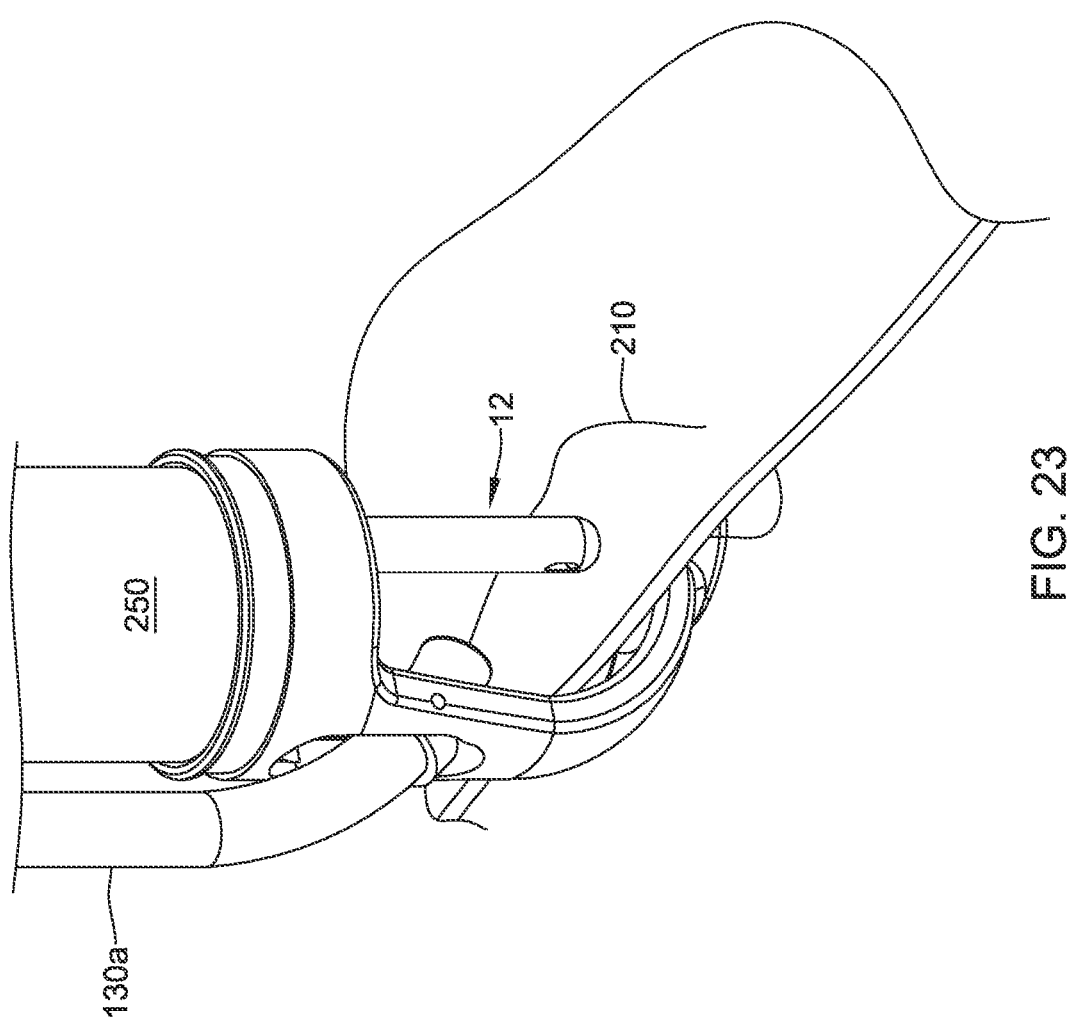
Figure 24:
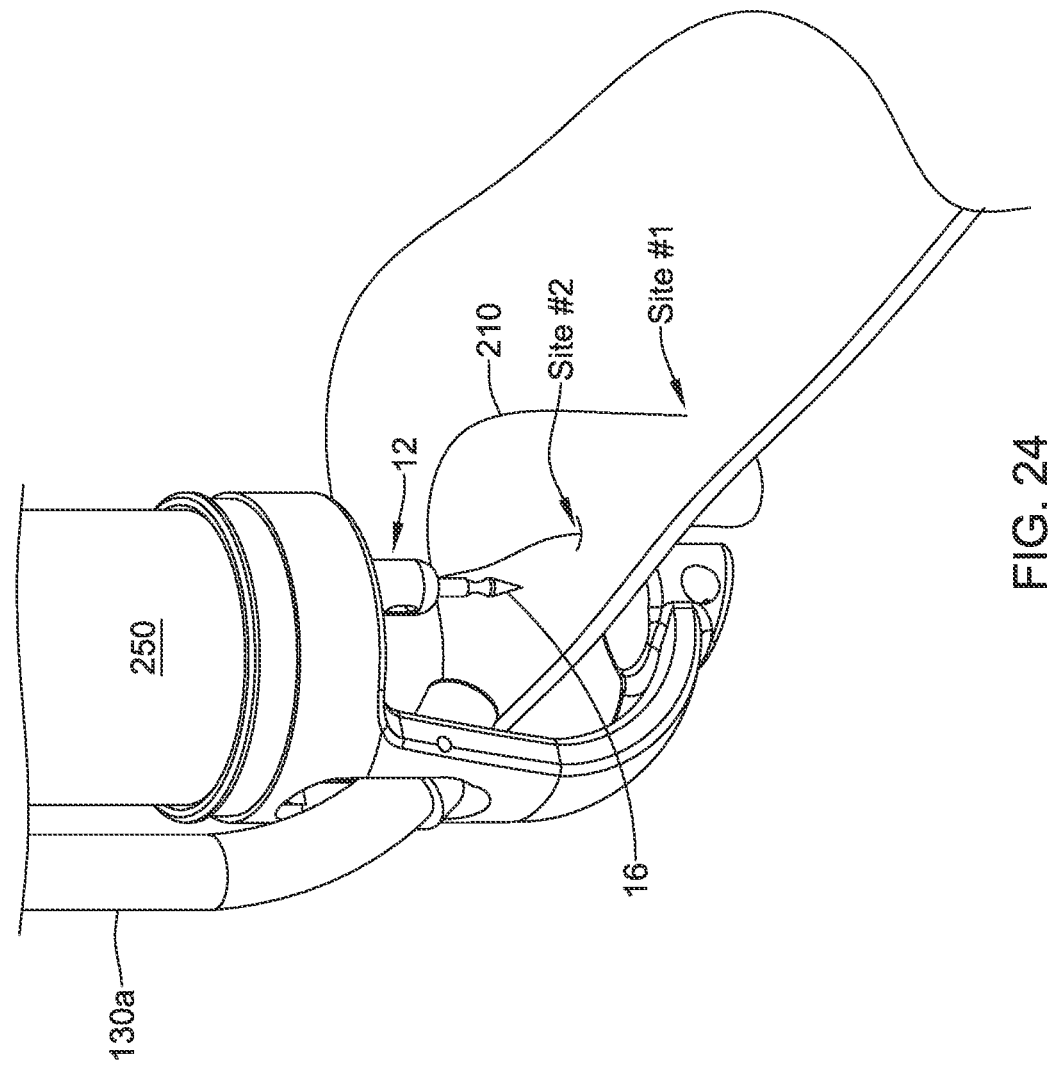
Figure 25:
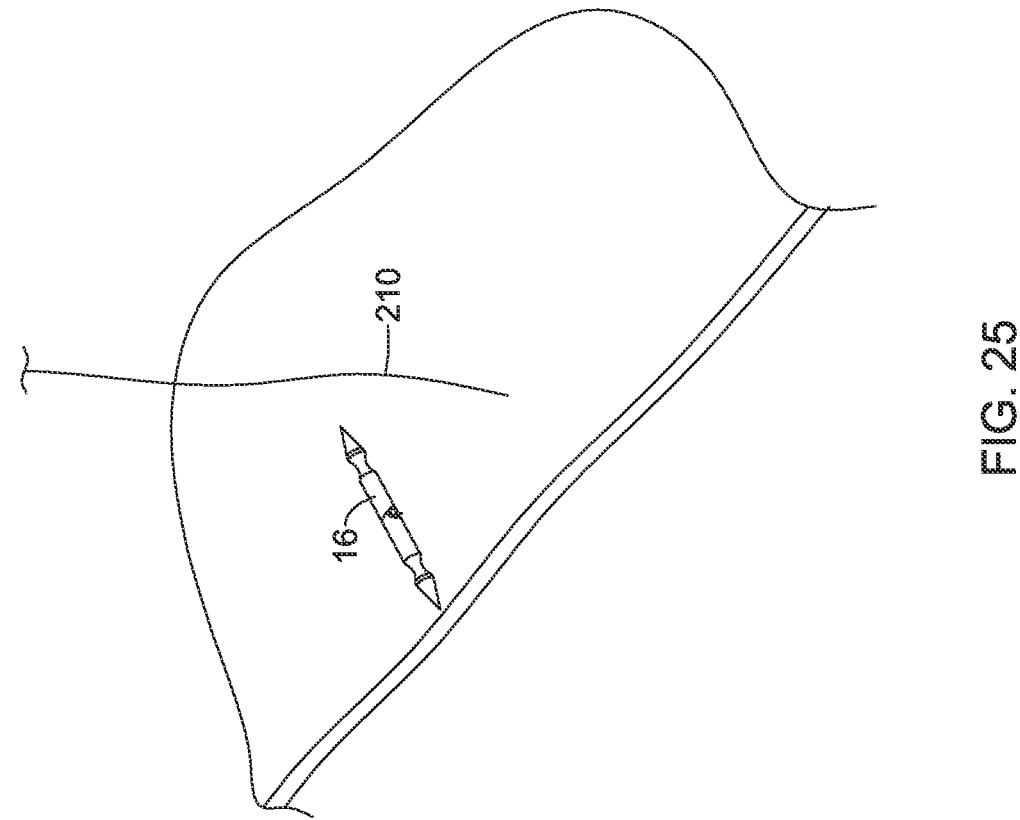

Moving to FIG. 22, the suture device 10 may be moved to the opposite side of the defect 200, with the needle 16 still locked into the endcap 34. The suture 210 is allowed to advance freely to provide sufficient play to create suture site #2. Moving to FIG. 23, the operator pushes the suture device 10 distally to push the tissue over the needle 16 while maintaining the translation handle 26 in an unlocked position. Once the suture translation element 12 is over the needle 16, the translation handle 26 is pushed distally to lock the needle 16 into the suture translation element 12. As seen in FIG. 24, the suture translation element 12 is pulled proximally to pull the rest of the needle 16 through the tissue. These steps are repeated until all suture sites are complete. In some cases, as shown in FIG. 25, the needle 16 may be used as an anchor for the last stitch. In some instances, the needle 16 may be biosorbable.

Figure 26:
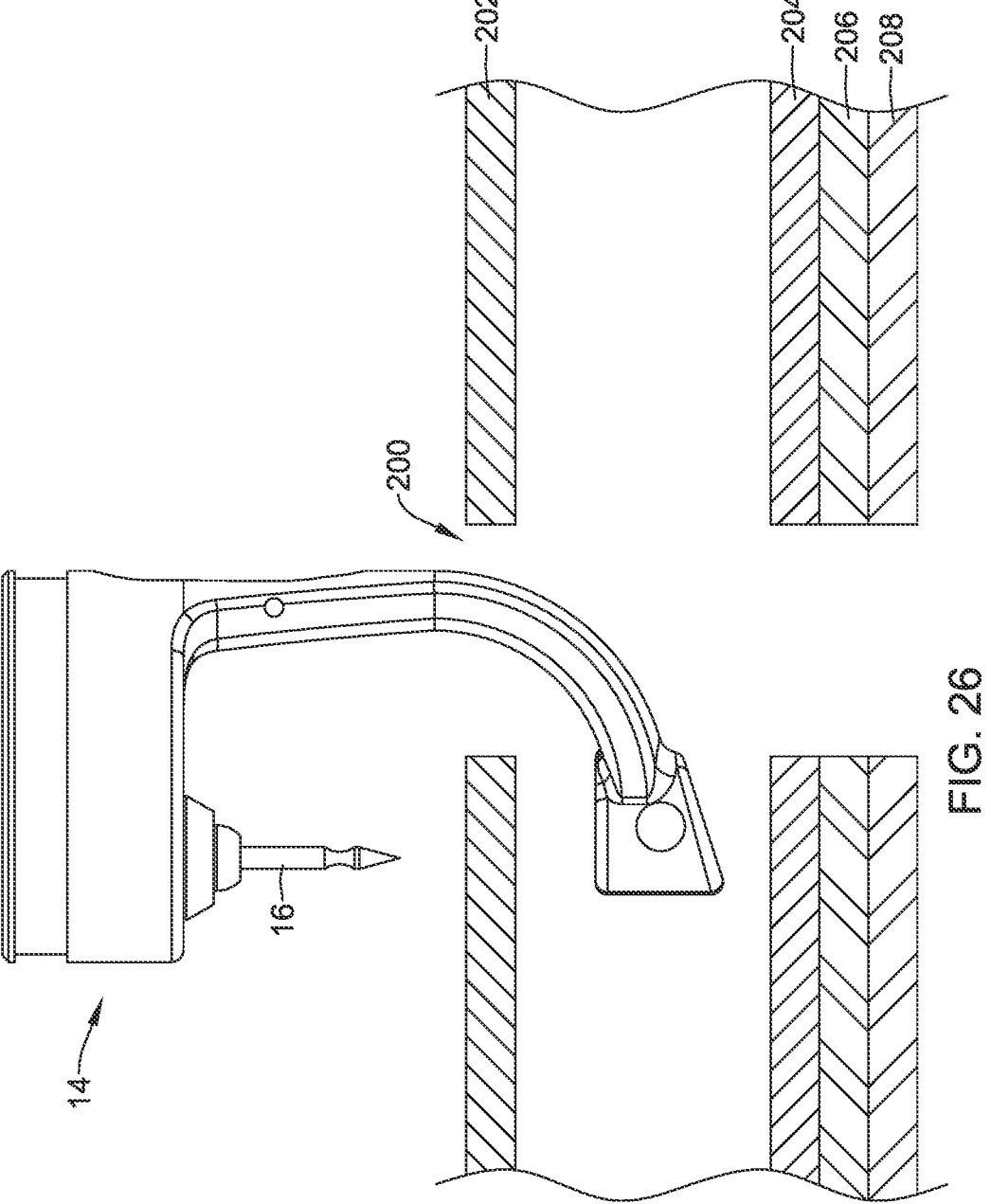
FIGS. 26 through 32 illustrate use of a suture device in a partial thickness procedure in accordance with an example of the disclosure.
Figure 27:
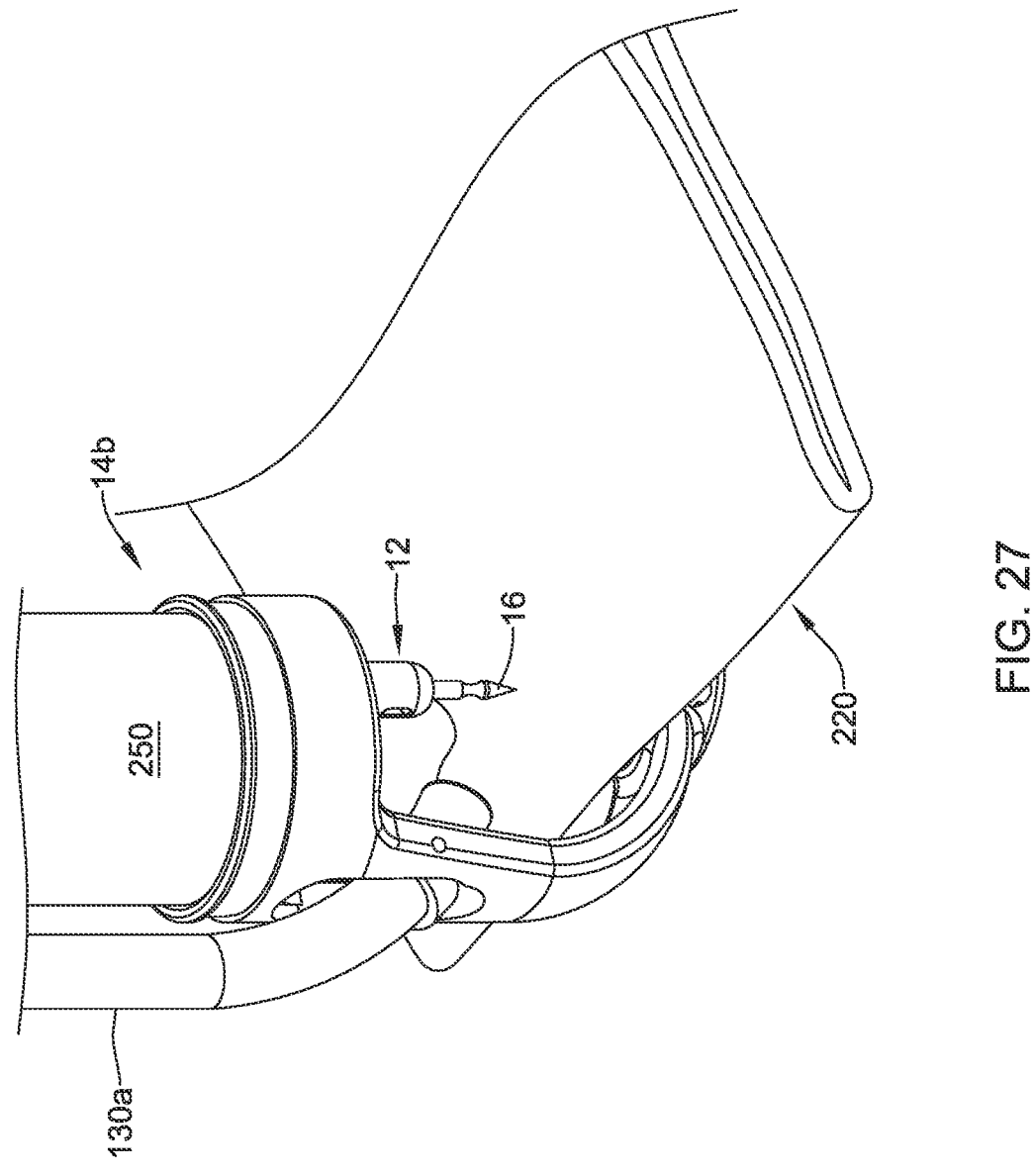
Figure 28:
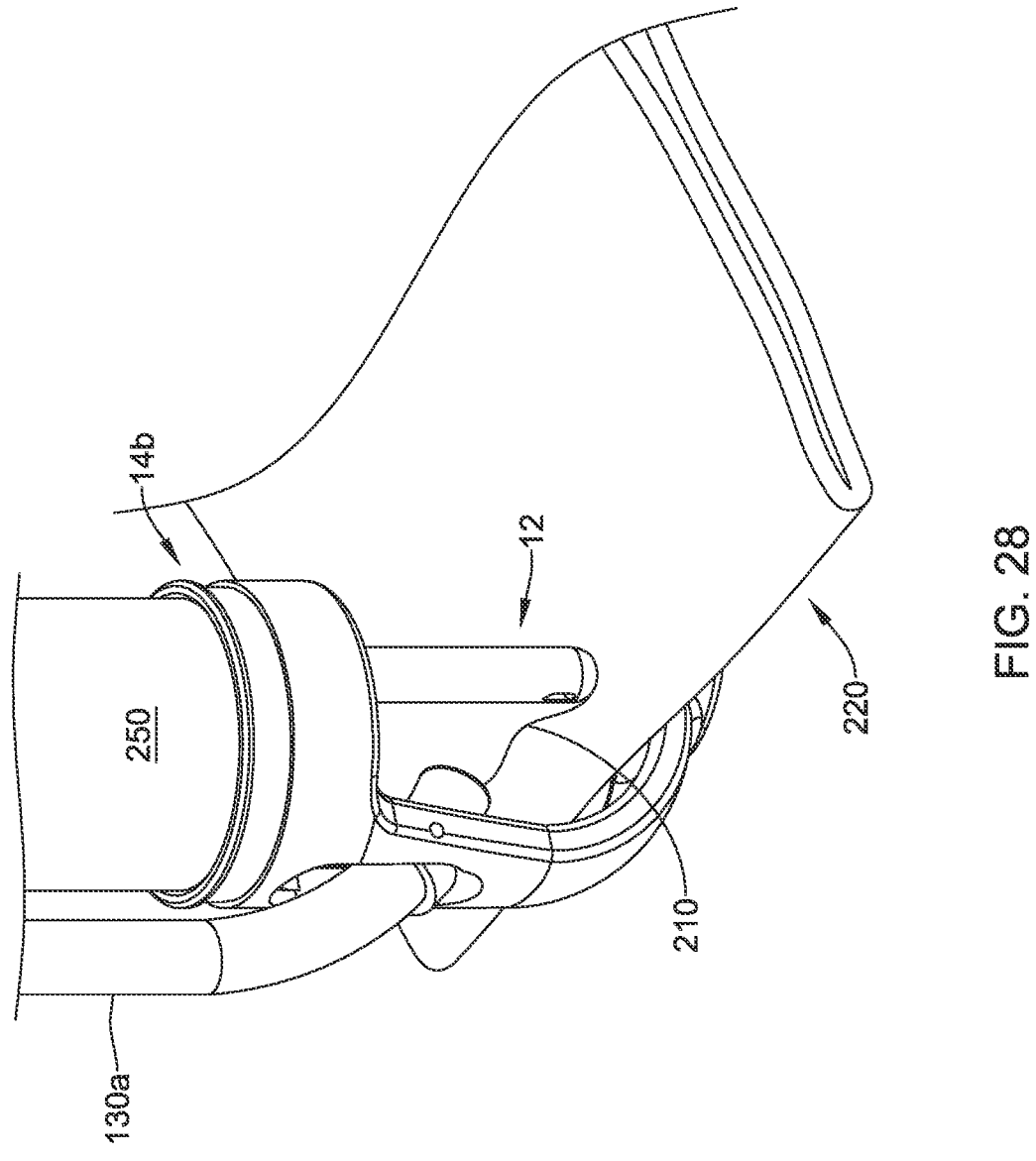

FIG. 26 shows the distal assembly 14 positioned relative to the defect 200, with the endcap 34 positioned between the mucosa layer 202 and the submucosa layer 204. In some cases, injection of a suitable fluid such as saline may provide working space between the layers. In this example, there is a desire to only approximate the mucosal layers 202. As seen in FIG. 27, the suture device 10 may be placed at one end of the defect 200, and a bleb 220 may be created where the tissue is doubled over on itself. With the needle 16 exposed, and with respect to FIG. 28, the suture translation element 12 may be pushed distally until the needle 16 passes through the tissue and locks into the endcap 34.

Figure 29:
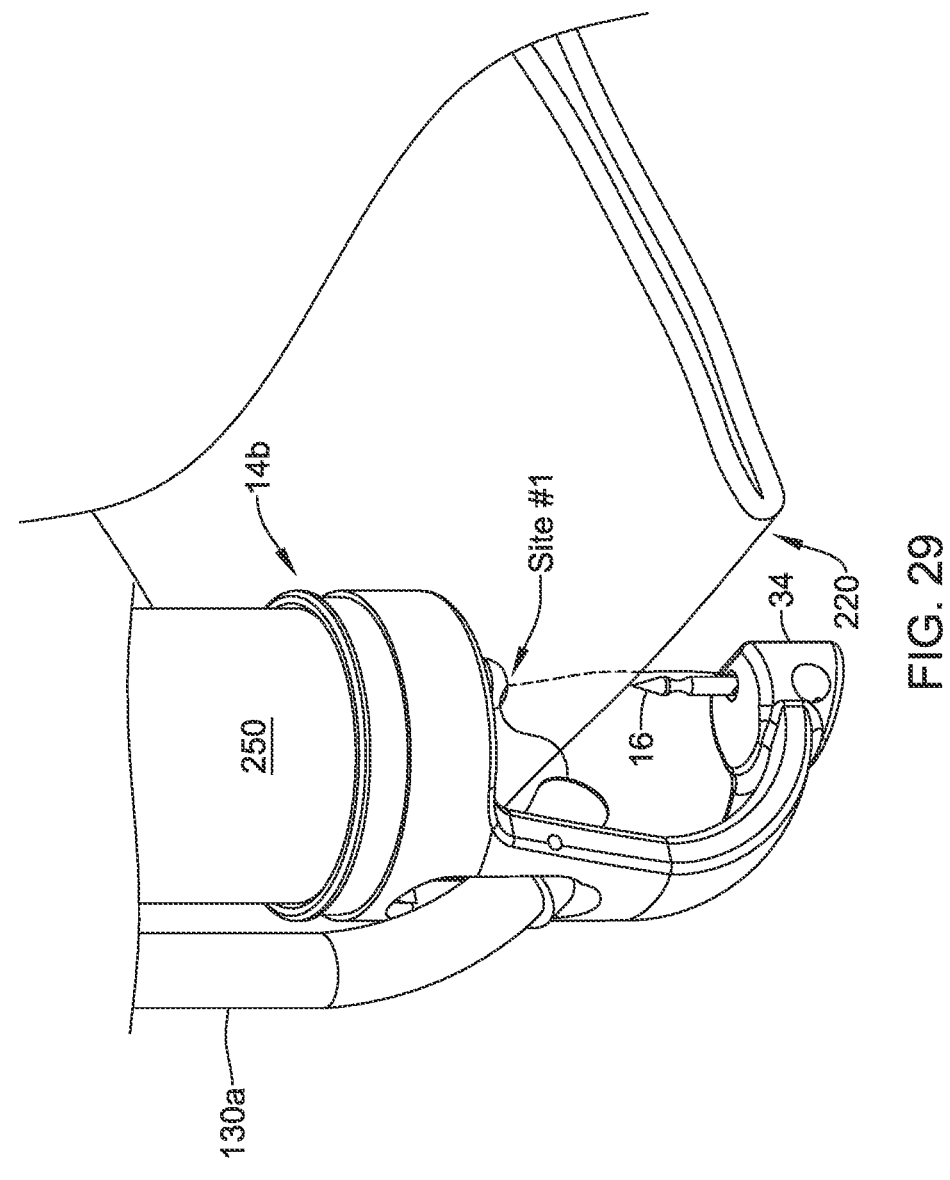
Figure 30:
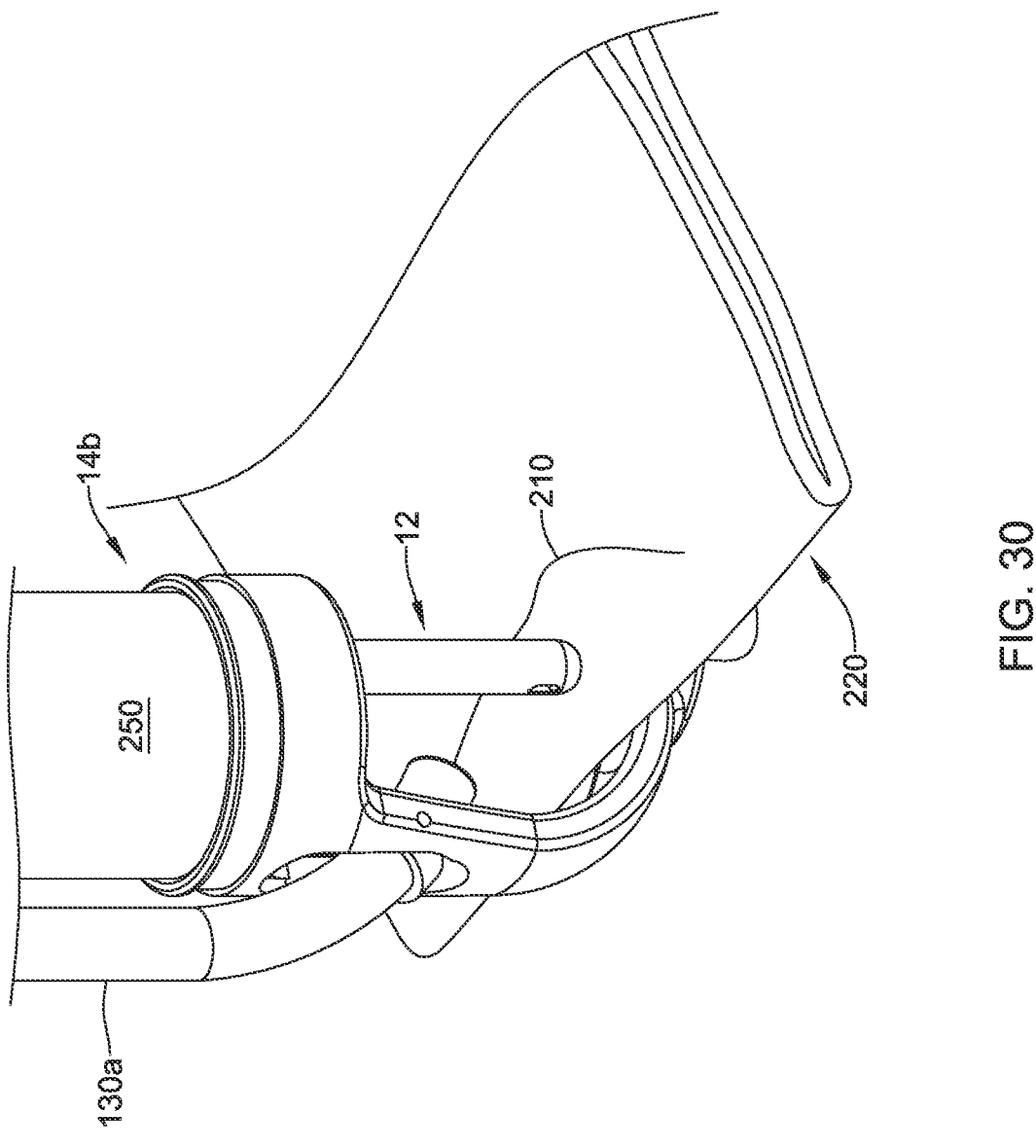
Figure 31:
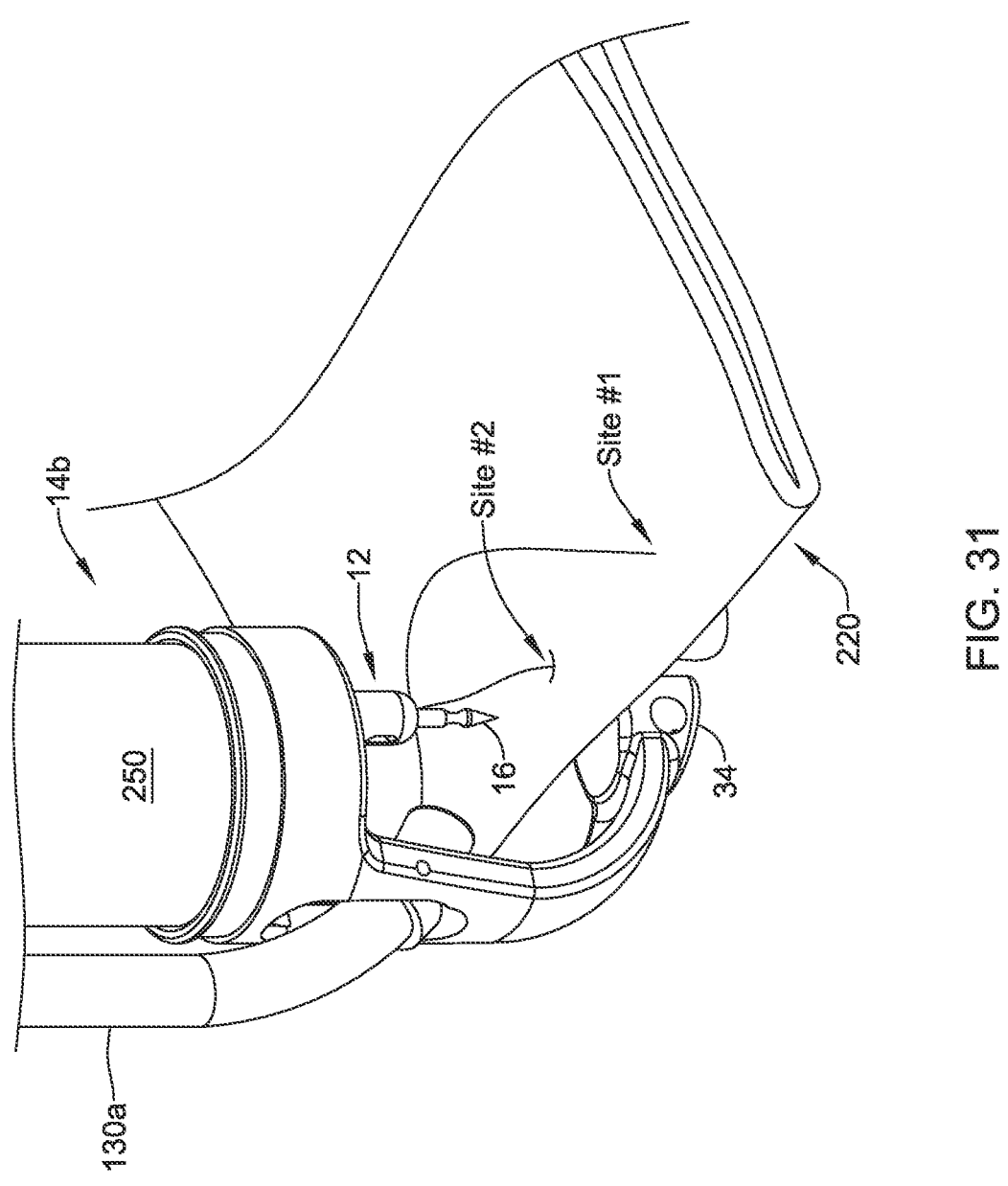
Figure 32:
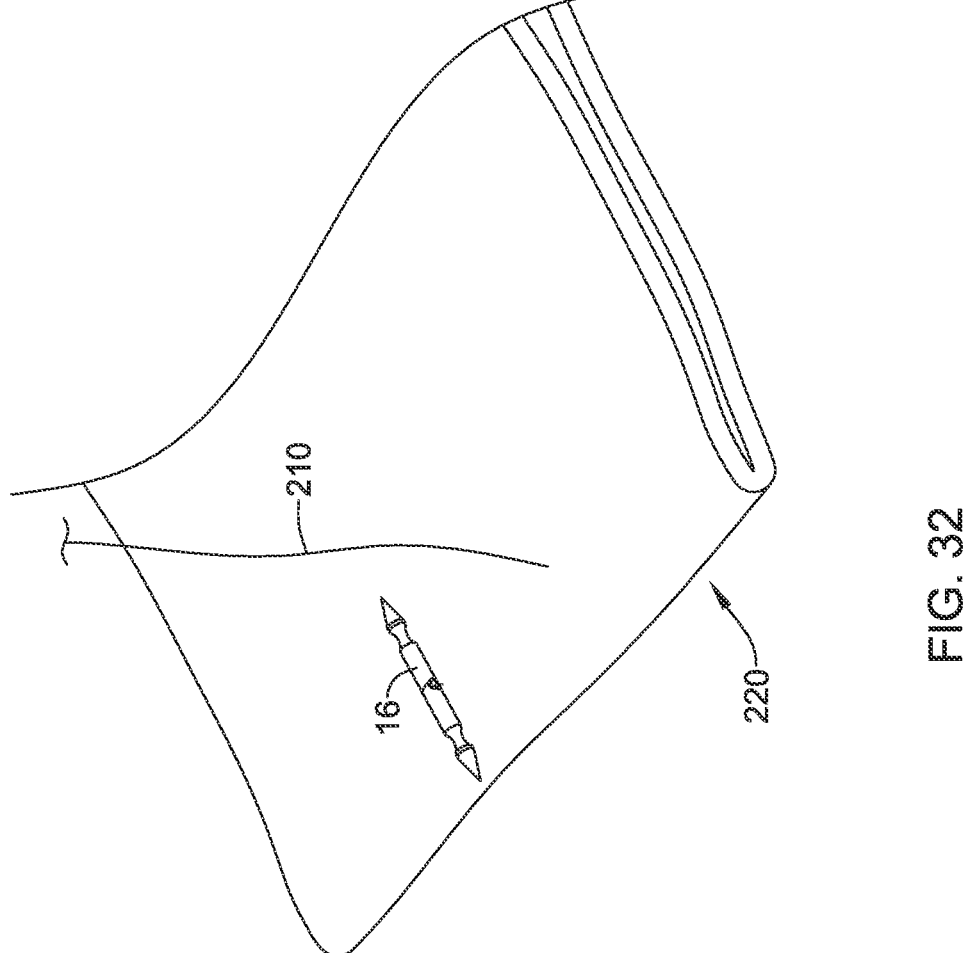

Next, and as seen in FIG. 29, with the needle 16 locked into the endcap 34, the user pulls on the translating handle 26 to unlock the needle 16 and to pull the suture translation element 12 proximally clear of the needle 16. The delivery device may be pushed distally to push the needle 16 completely through the tissue. This completes suture site #1. The suture device 10 is moved to a new suture site, as seen in FIG. 30, with the needle 16 still locked into the endcap 34. Suture 210 is allowed to advance freely to provide sufficient play to create suture site #2. Another bleb 220 of tissue is formed. As seen in FIG. 31, the operator pushes the suture device 10 distally to push the tissue over the needle 16 while maintaining the translating handle 26 in the unlocked position. Once the suture translation element 12 is over the needle 16, the translating handle 26 may be pushed distally to lock the needle 16 into the suture translation element 12. The suture translation element 12 then is pulled proximally to pull the needle 16 through the tissue. These steps continue until the defect 200 has been closed. In some cases, as shown in FIG. 32, the needle 16 may be used as an anchor for the last stitch.

Figure 33:
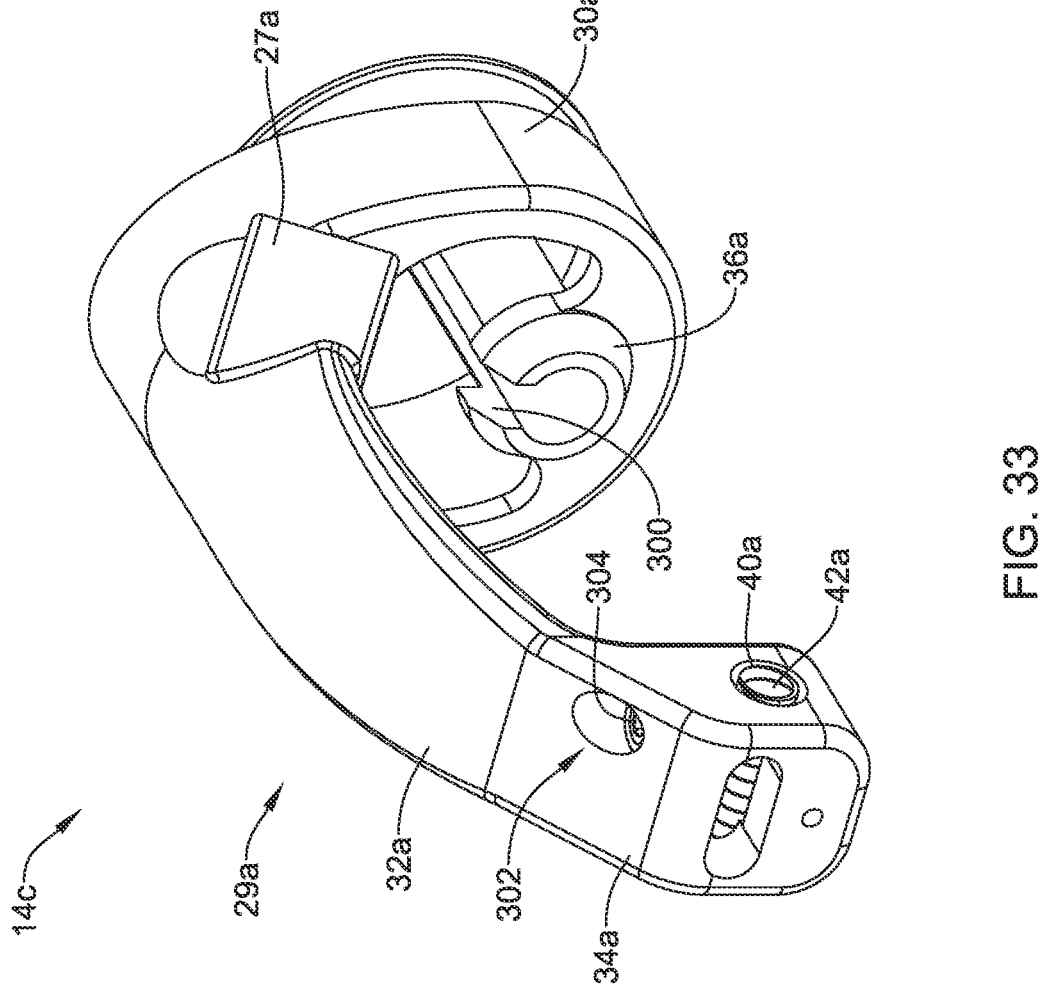
FIG. 33 is a perspective view of a distal assembly usable in the suture device of FIG. 1 in accordance with an example of the disclosure.

FIG. 33 is a perspective view of a distal assembly 14c that may, for example, be usable in the suture device 10 shown in FIG. 1. The distal assembly 14c is similar to the distal assembly 14 shown in previous Figures, but includes several modifications that may be useful, particularly in bariatric revision procedures. A bariatric procedure commonly refers to a procedure in which the effective useful volume of a patient's stomach may be surgically reduced in order to effect long-term weight loss for the patient and may be performed laparoscopically. A bariatric revision procedure is a procedure, performed endoscopically, in which changes may be made to what was originally done to the patient's stomach. In some cases, the distal assembly 14c may also be used in other suturing procedures, such as but not limited to the full tissue thickness procedure shown in FIGS. 18 through 25 and/or the partial tissue thickness shown in FIGS. 26 through 32. These are just illustrative examples of the use of the distal assembly 14c. FIGS. 43 through 47, to be discussed subsequently, provide an example of a tangential approach useful in bariatric revision procedures.

The distal assembly 14c may include a body 29a having a proximal connector 30a that may be configured to be coupled to the distal end of an endoscope or other delivery system, for example. The body 29a includes an arm 32a that extends to an endcap 34a. In some cases, the body 29a, including the arm 32a, may be similar to the body 29 and arm 32 referenced previously with respect to the distal assembly 14, the distal assembly 14a and the distal assembly 14b. In some instances, however, the body 29a and the arm 32a may be adapted to accommodate thicker tissue, which may for example mean a change in the overall shape of the body 29a and/or the arm 32a relative to the body 29 and/or the arm 32. In some cases, the body 29a and/or the arm 32a may simply be larger in order to accommodate thicker tissue. The distal assembly 14c may be considered as including a guide member 36a that may be secured to or integrally formed with the body 29a, and may be configured to permit a suture translation assembly (such as the suture translation assembly 12, a suture translation assembly 12a, shown in FIGS. 34 through 38, or a suture translation assembly 12b, shown in FIG. 39 through FIG. 42) to extend through the guide member 36a and to translate relative to the guide member 36a.

In some cases, as illustrated, the guide member 36a includes a channel 300. In some cases, the channel 300 permits a suture to pass between the suture translation assembly 12, 12a, 12b and a working channel of the endoscope or other delivery device to which the distal assembly 14c is attached. The channel 300 may, for example, be designed to include a lead in that would help to align the suture with the channel 300 when passing the suture translation assembly 12, 12a, 12b through the working channel of the endoscope or other delivery device. In some cases, there may be a desire to load the suture before passing the suture translation assembly 12, 12a, 12b through the working channel of the endoscope or other delivery device.

In some instances, the distal assembly 14c includes a guide structure 27a that is attached to or integrally formed with the body 29a. In some cases, the guide structure 27a may instead be pivotably attached to the body 29a. The guide structure 27a may be configured to accommodate a polymeric tubular member attached thereof, in order to guide tools through the endoscope and into position relative to the working site. In some instances, the guide structure 27a may be configured to accommodate a metallic tubular member attached thereto. In some cases, for example, the guide structure 27a and accompanying tubular member (not illustrated) may accommodate a graspers or similar tool that allows a user to grasp tissue and pull it into position so that the needle 16 may be passed through the tissue. In some cases, the relative position, or offset of the guide structure 27a, relative to the relative position or offset illustrated with respect to the distal assembly 14, the distal assembly 14a or the distal assembly 14b, may be greater in order to provide more room for tools and/or to accommodate larger and/or thicker portions of tissue.

The end cap 34a includes one or more securement openings 40a that may be, as can be seen, be arranged orthogonally to a proximal needle opening (not illustrated), such as the proximal needle opening 37 illustrated for example in FIG. 3. One or more securements 42a may correspondingly be disposed within the one or more securement openings 40a. In some cases, the one or more securements 42a may be a coil spring that is disposed within the one or more securement openings 40a. The securement 42a may releasably engage a detent on the needle 16, as discussed with respect to the distal assembly 14.

In some cases, the securement opening 40a visible on the right side (in the illustrated orientation) may have a diameter that is greater than an overall diameter of the securement 42a and the securement opening 40a may taper to a diameter on the left side (not seen) that is about the same as the diameter of the securement 42a. In some cases, the securement 42a may be welded, soldered, adhesively secured or otherwise attached at the left side of the securement opening 40a, and may be free to move somewhat at the right side of the securement opening 40a. In some instances, the distal assembly 14c may include an opening 302 that is orthogonal to the securement opening 40a. The opening 302 may be threaded in order to threadedly engage a set screw 304. In some cases, as illustrated, the opening 302 may be offset closer to the right side of the securement opening 40a, away from the secured end of the securement 42a, such that the set screw 304 may be considered as supporting the free end of the securement 42a. Rotating the set screw 304 in a first direction, such as clockwise, may cause the set screw 304 to translate towards the securement 42a, thereby increasing an interference between the securement 42a and the needle 16 and increasing a retentive force that can be applied to the needle 16. Conversely, rotating the set screw in a second direction, such as counter-clockwise, may cause the set screw 304 to translate away from the securement 42a, thereby decreasing the retentive force that can be applied to the needle 16. This may help to adjust for manufacturing tolerances, for example.

Figure 34:
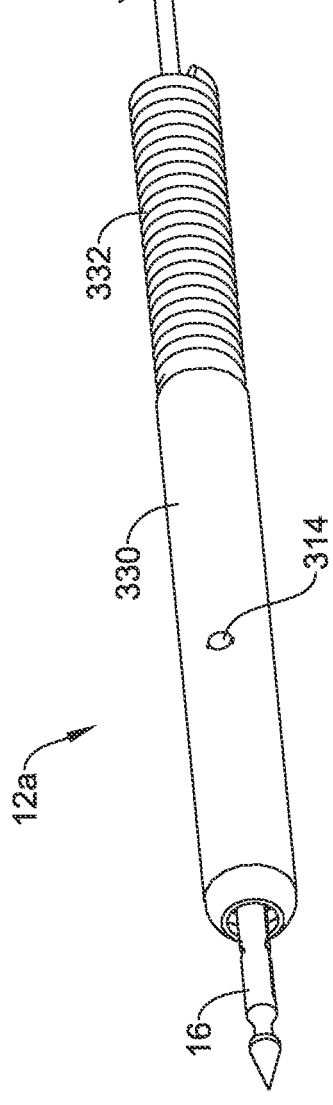
FIG. 34 is a perspective view of a suture translation assembly usable in the suture device of FIG. 1 in accordance with an example of the disclosure.
Figure 35:
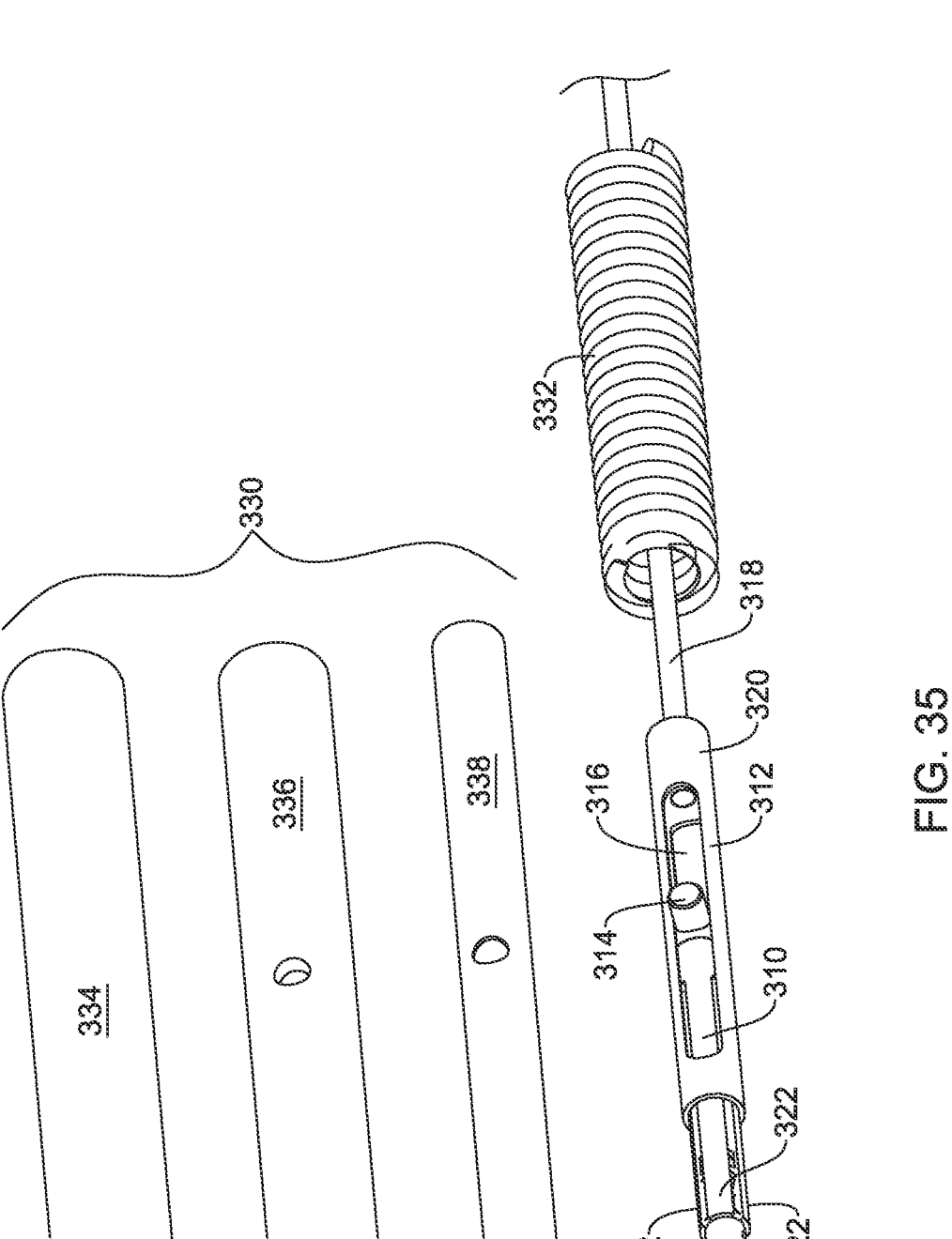
FIG. 35 is a partially exploded perspective view of the suture translation assembly of FIG. 34 in accordance with an example of the disclosure.

As noted, the distal assembly 14c may be used in combination with the suture translation assembly 12 discussed previously with respect to FIG. 5, for example. The distal assembly 14c may also be used with a suture translation assembly 12a, shown in FIG. 34 through FIG. 38, as well as with a suture translation assembly 12b, shown in FIG. 39 through FIG. 42. FIG. 34 is a perspective view of the suture translation assembly 12a, shown holding the needle 16, while FIG. 35 is a partially exploded view of the suture translation assembly 12a. As better seen in FIG. 31, the suture translation assembly 12a includes an inner member 310 that hold the needle 16. A locking member 312 is slidingly disposed over the inner member 310. As can be seen, the inner member 310 includes a pin 314 that extends radially outwardly from the inner member 310 and extends through a corresponding slot 316 that is formed in the locking member 312. The pin 314 serves to prevent relative rotation between the inner member 310 and the locking member 312. The pin 314 also serves to limit translation of the locking member 312 relative to the inner member 310.

A control member 318 is secured relative to a proximal end 320 of the locking member 312, and extends distally to a handle such as the translating handle 26 (FIG. 1). As a result, the locking member 312 may be translated distally and/or proximally relative to the inner member 310. As seen in FIG. 34, the suture translation assembly 12a includes an outer sleeve 330 that may be pinned via the pin 314 to the inner member 310. The outer sleeve 330 may be coupled with a coil 332, for example. In some cases, the outer sleeve 330 may be a single tubular member. In some cases, as shown for example in FIG. 35, the outer sleeve 330 may actually include one or more of an outer sleeve 334, a slotted sleeve 336, and an inner outer sleeve 338. The slotted sleeve 336 may be configured to permit a suture to pass therethrough. This is merely illustrative, and is not intended to be limiting in any fashion.

Figure 36:
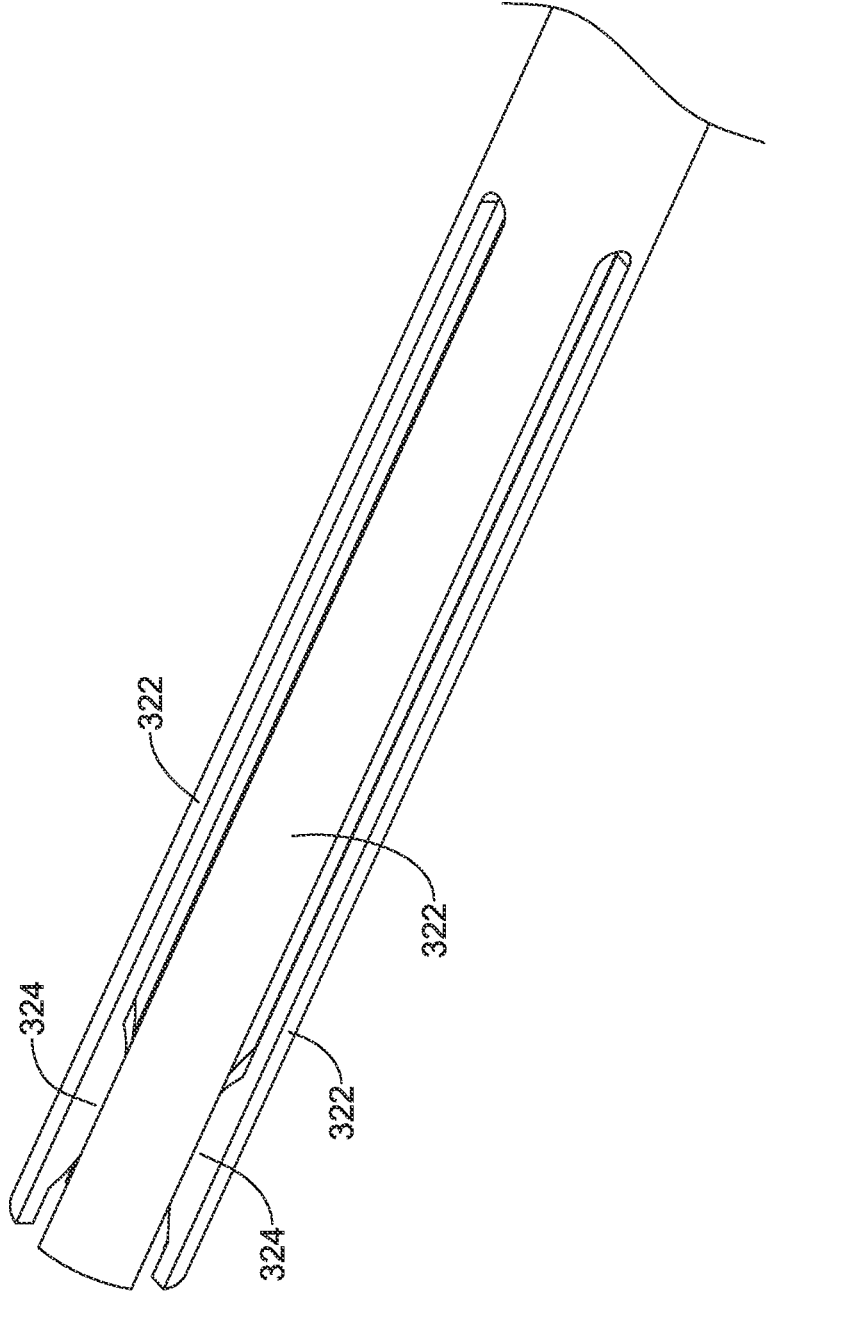
FIG. 36 is a perspective view of an inner member forming a portion of the suture translation assembly of FIG. 34 in accordance with an example of the disclosure.
Figure 37:
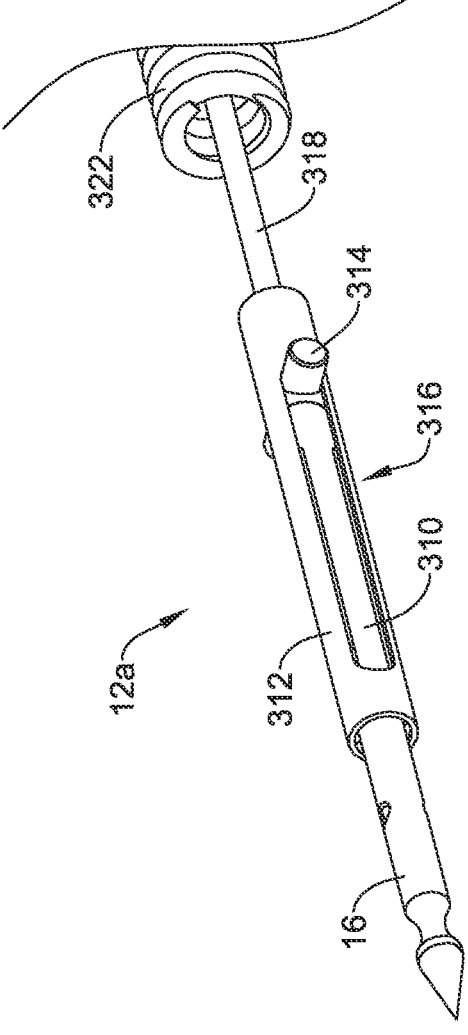
FIG. 37 is a perspective view of a portion of the suture translation assembly of FIG. 34, shown in a locked configuration in accordance with an example of the disclosure.
Figure 38:
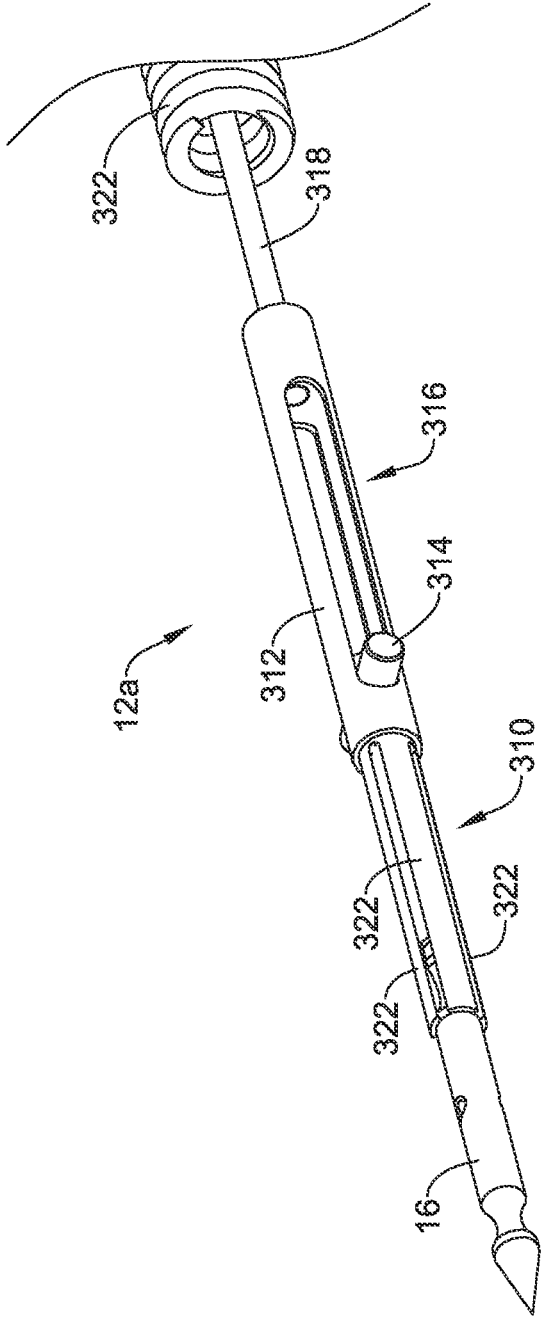
FIG. 38 is a perspective view of a portion of the suture translation assembly of FIG. 34, shown in an unlocked configuration in accordance with an example of the disclosure.

The inner member 310 includes several arms 322 that, as seen in FIG. 36, which shows the distal portion of the inner member 310, include curved tabs 324 that are configured to engage corresponding detents within the needle 16. While a total of four arms 322 are shown, it will be appreciated that the inner member 310 may include any number of arms 322. It will be appreciated that the arms 322 are relatively long in length, and as a result may be considered as being relatively flexible. With the locking member 312 extended distally into a locking configuration, as shown for example in FIG. 37, the locking member 312 prevents outward movement of the arms 322. As a result, the curved tabs 324 remain in engagement with the corresponding detents of the needle 16, and the needle 16 remains locked to the suture translation assembly 12a. With the locking member 312 retracted proximally into an unlocked configuration, as shown for example in FIG. 38, the arms 322 are free to move radially outwardly, thereby releasing the curved tabs 324 from the detents in the needle 16, and allowing the needle 16 to move distally relative to the inner member 310.

Figure 39:
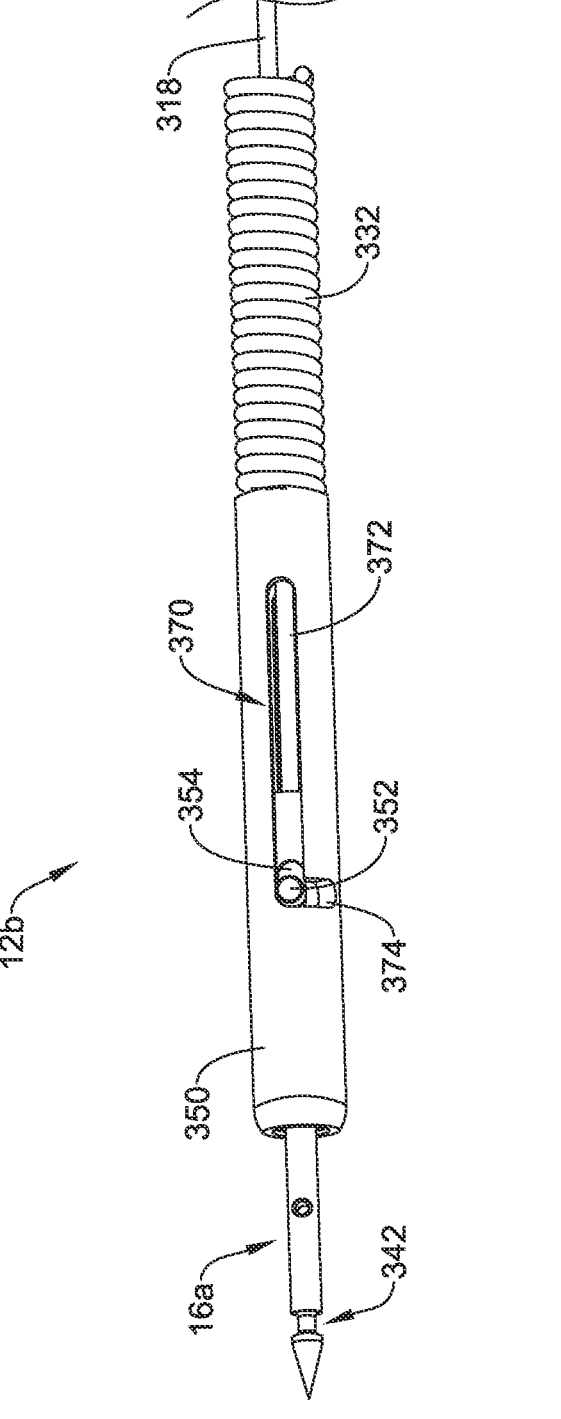
FIG. 39 is a perspective view of a suture translation assembly usable in the suture device of FIG. 1 in accordance with an example of the disclosure.
Figure 40:
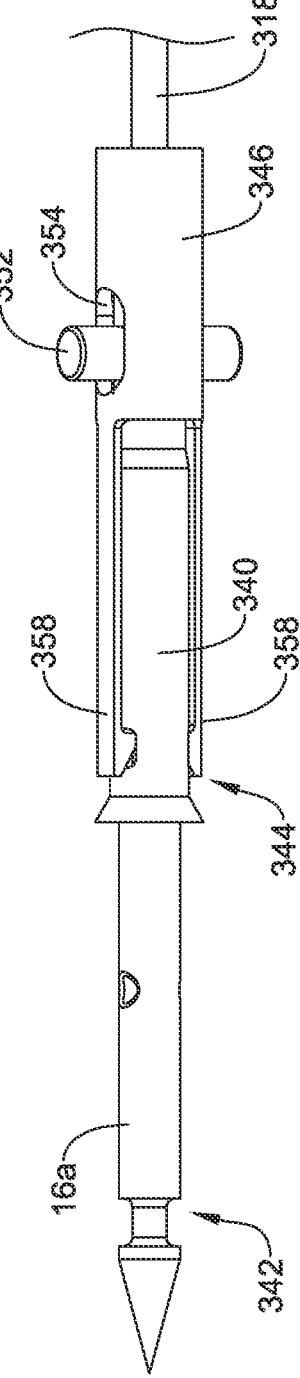
FIG. 40 is a perspective view of the suture translation assembly of FIG. 39, shown with some elements removed to show internal structure, with the suture translation assembly shown in a locked configuration in accordance with an example of the disclosure.

FIG. 39 is a perspective view of a suture translation assembly 12b that may be used in combination with any of the distal assembly 14, the distal assembly 14a, the distal assembly 14b and/or the distal assembly 14c. FIG. 40 is a perspective view of the suture translation assembly 12b with outer portions such as an outer sleeve 350 (FIG. 39) removed to reveal an inner member 340 that holds a needle 16a. In some cases, the outer sleeve 350 may be a single tubular member. In some instances, the outer sleeve 350 may include several elements, such as described with respect to the outer sleeve 330 (FIG. 35).

In some cases, as illustrated, the needle 16a has a distal detent 342 and a proximal detent 344 (visible in FIG. 41) that are shaped differently than the corresponding detents in the needle 16. The suture translation assembly 12b includes a locking member 346 that is slidingly disposable relative to the inner member 340. The pin 352 is attached to the inner member 340 and extends through a corresponding slot 354 formed in the locking member 342. The pin 352 limits translation of the locking member 342 relative to the inner member 340, and also prevents relative rotational movement of the locking member 342. The locking member 342 is secured to the control member 318, which extends distally to a handle such as the translating handle 26 (FIG. 1). As a result, the locking member 342 may be translated distally and/or proximally relative to the inner member 340.

In some cases, the outer sleeve 350 may define a slot 370 including an axially extending slot portion 372 and a shorter radially extending slot portion 374. In some cases, the axially extending slot portion 372 permits the pin 352 to move within the axially extending slot portion 372 in order to permit the needle 16a to be fully withdrawn into the suture translation assembly 12b for advancement through an endoscope or other delivery device. Once the suture translation assembly 12b has been advanced through the endoscope or other delivery device, the inner member 340 and the locking member 342 may be advanced distally through the outer sleeve 350 until the pin 352 aligns with the radially extending slot portion 374. By rotating the translating handle 26, the pin 352 may be rotated into position within the radially extending slot portion 374 so that the locking member 342 may be translated relative to the inner member 340.

Figure 41:
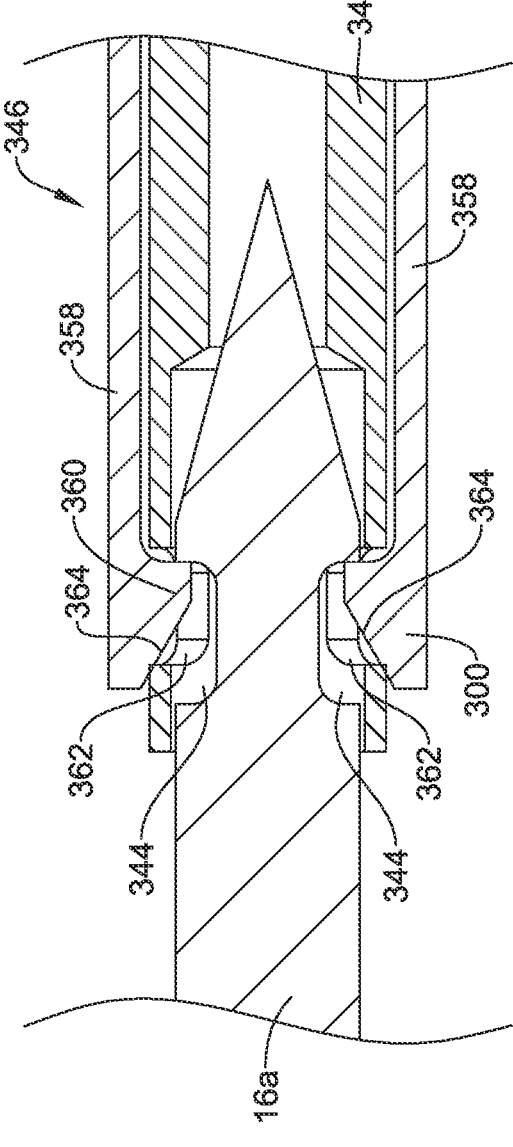
FIG. 41 is a side view of a portion of the suture translation assembly of FIG. 39, showing how a locking member engages an inner member of the suture translation assembly and a needle in the locked configuration as shown in FIG. 40 and in accordance with an example of the disclosure.

In some cases, as illustrated, the locking member 342 includes a pair of arms 358 that extend distally from the locking member 342. As seen for example in FIG. 41, the arms 358 include tabs 360 that, when the suture translation assembly 12b is in a locked configuration as shown in FIGS. 40 and 41, the tabs 360 extend through slots 362 formed within the inner member 340. As a result, the tabs 360 are able to extend through the slots 362 and engage the proximal detent 344 of the needle 16a. While a pair of arms 358 are illustrated, it will be appreciated that the locking member 342 may include any number of arms 358, and of course a corresponding number of slots 362.

Figure 42:
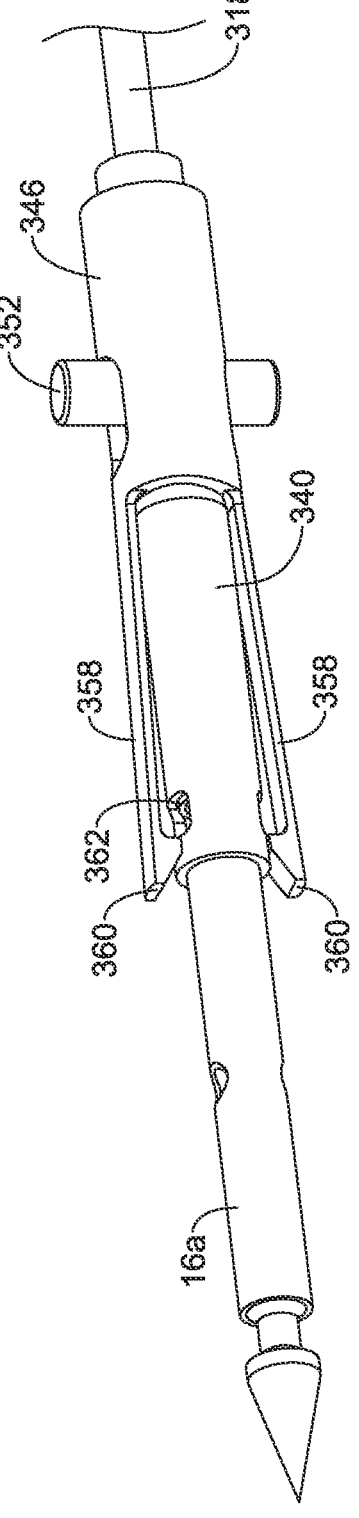
FIG. 42 is a perspective view of the suture translation assembly of FIG. 39, shown in an unlocked configuration in accordance with an example of the disclosure.

In order to move the suture translation assembly 12*b* into an unlocked configuration, as shown for example in FIG. 42, the locking member 342 may be moved distally relative to the inner member 340. As can be seen in FIG. 42, the tabs 360 have moved out of the slots 362 (only one slot 362 is seen), and the needle 16*a* is free to move relative to the suture translation assembly 12*b*. As the locking member 342 moves distally, angled surfaces 364 push against the slots 362 and are moved outwardly.

Figure 43:
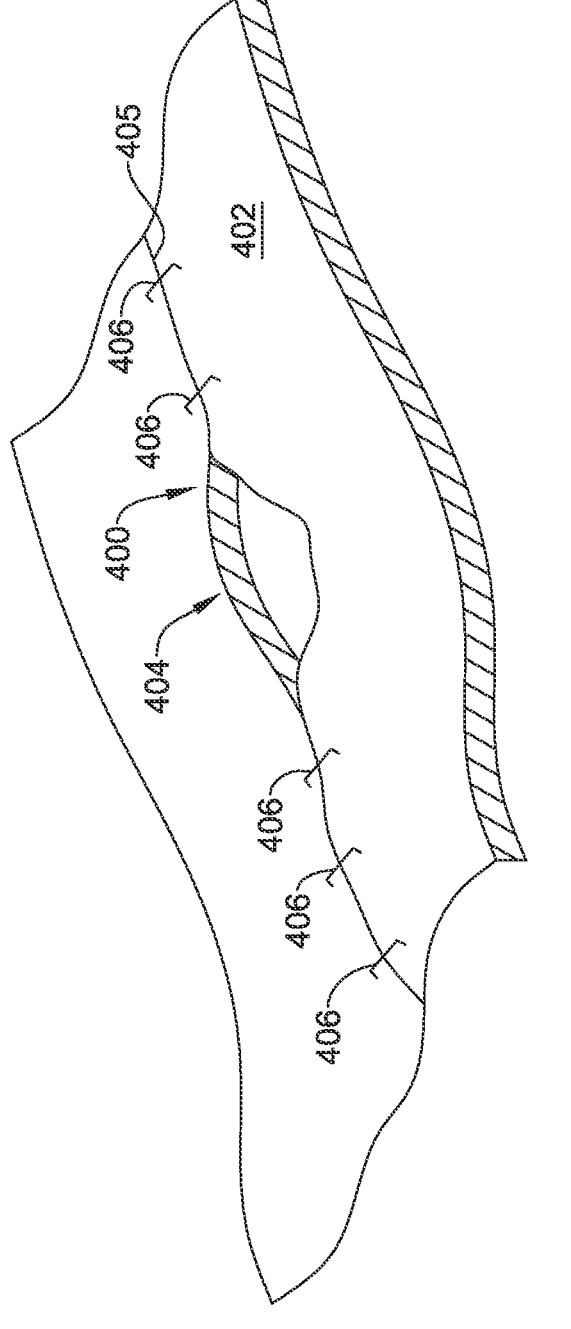
FIGS. 43 through 47 illustrate use of a suture device in a tangential approach that may be used in suturing thicker tissue and/or larger wounds such as those encountered during a bariatric revision procedure in accordance with an example of the disclosure.

FIGS. 43 through 47 provide an illustrative but non-limiting example of the distal assembly 14*c* being used to perform a tissue repair using a tangential approach. A tangential approach may be used, for example, when repairing a larger wound that requires suturing through thicker or more tissue. Bariatric revision procedures are an example of a procedure that would benefit from a tangential approach. It will be appreciated that the distal assembly 14*c*, in performing the illustrated procedure, may be secured to the distal end of an endoscope or other delivery device, and may be used in combination with any of the suture translation assembly 12, the suture translation assembly 12*a* and/or the suture translation assembly 12*b*, as desired. FIG. 43 shows a defect 400 within tissue 402. In some cases, the defect 400 may include a remaining open portion 404 along a staple or suture line 405. In some instances, a portion of the defect 400 has already been closed using staples 406, and in some cases the remaining open portion 404 may be positioned such that stapling is either inappropriate or difficult to perform.

Figure 44:
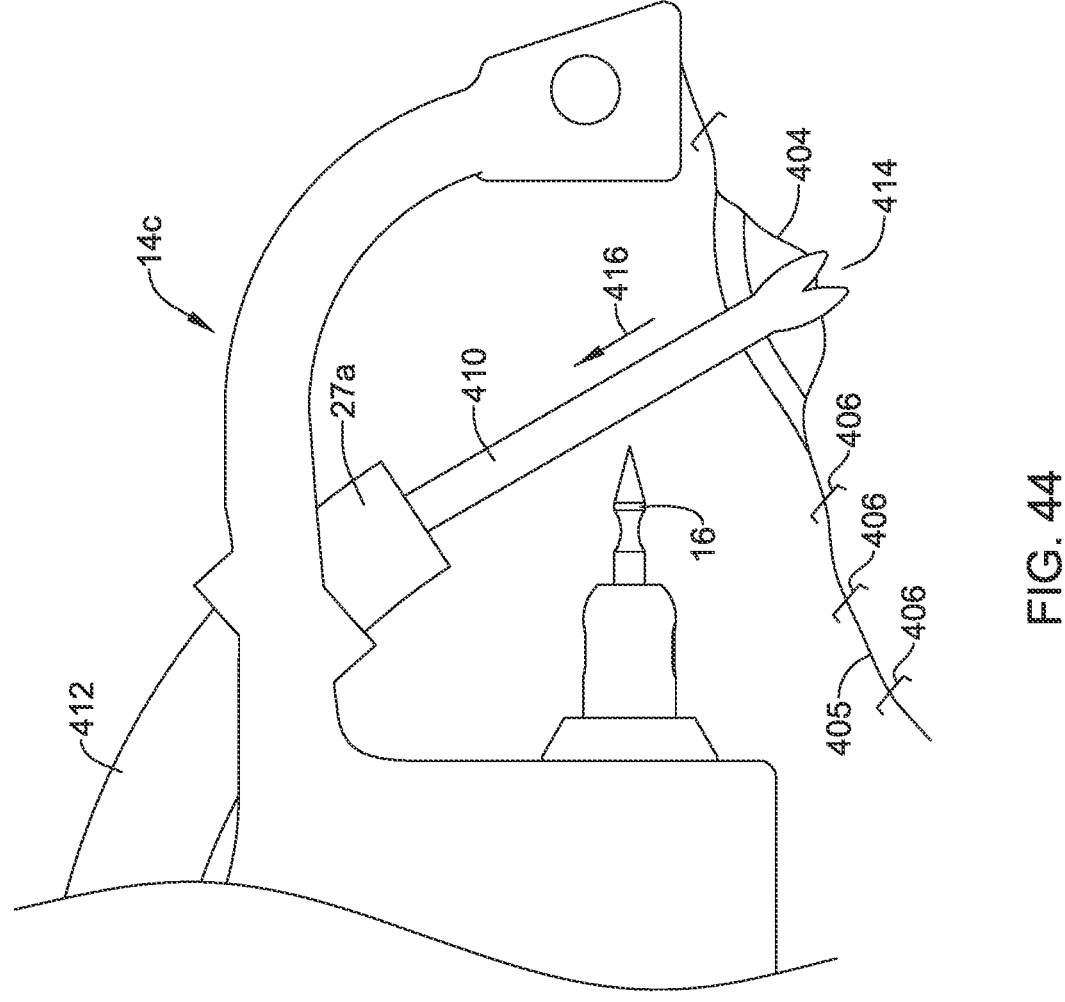
Figure 45:
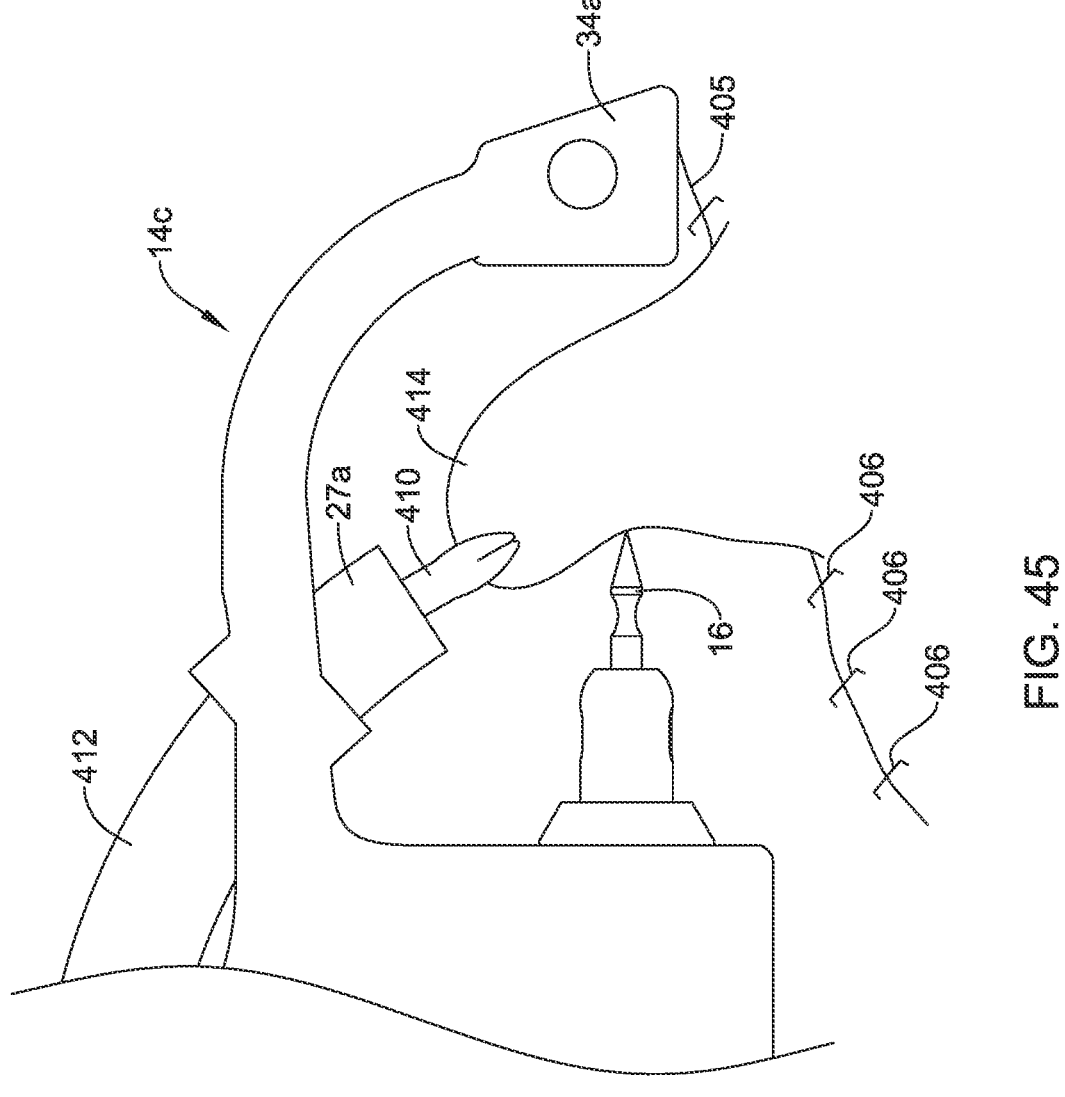
Figure 46:
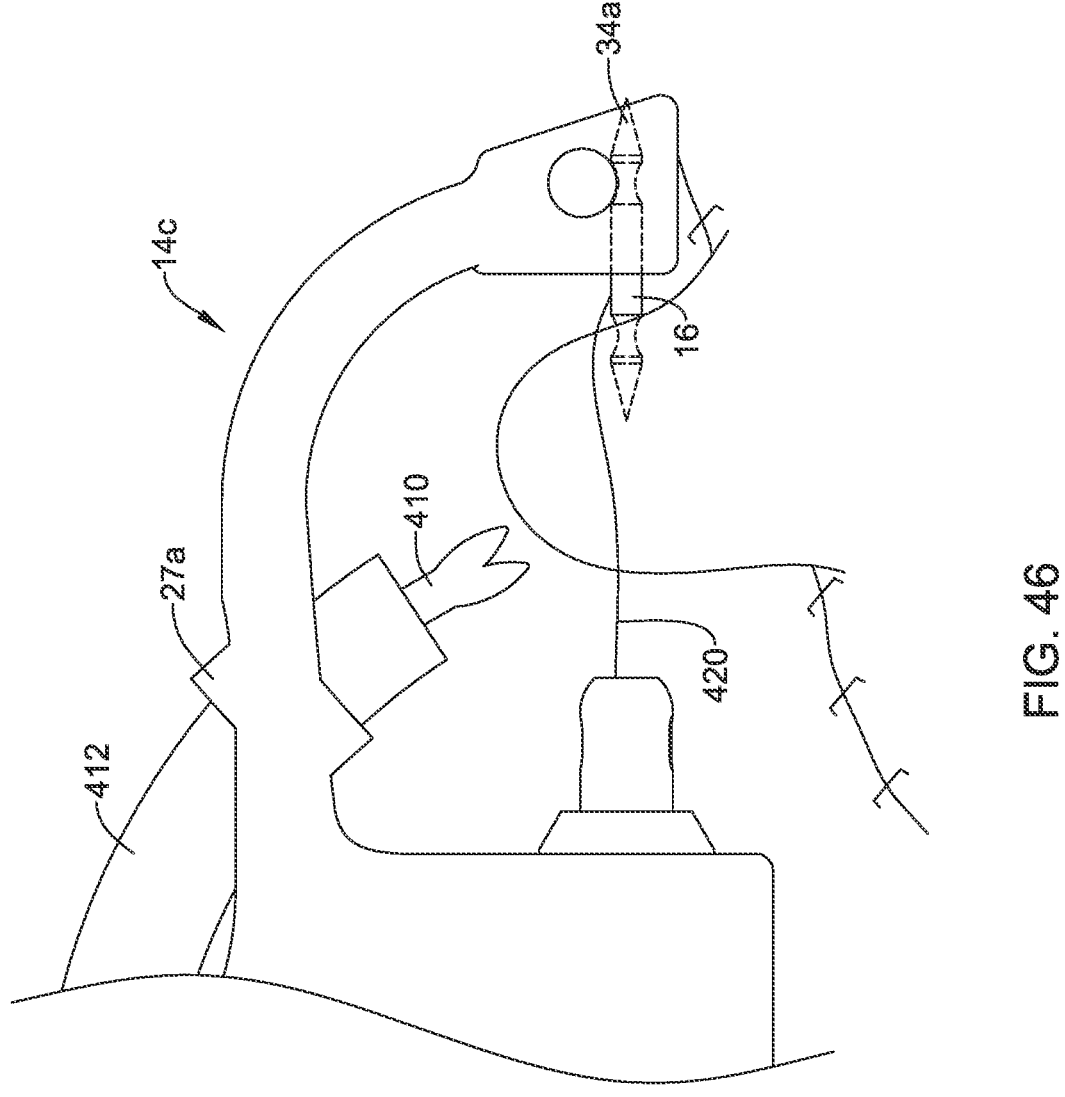
Figure 47:
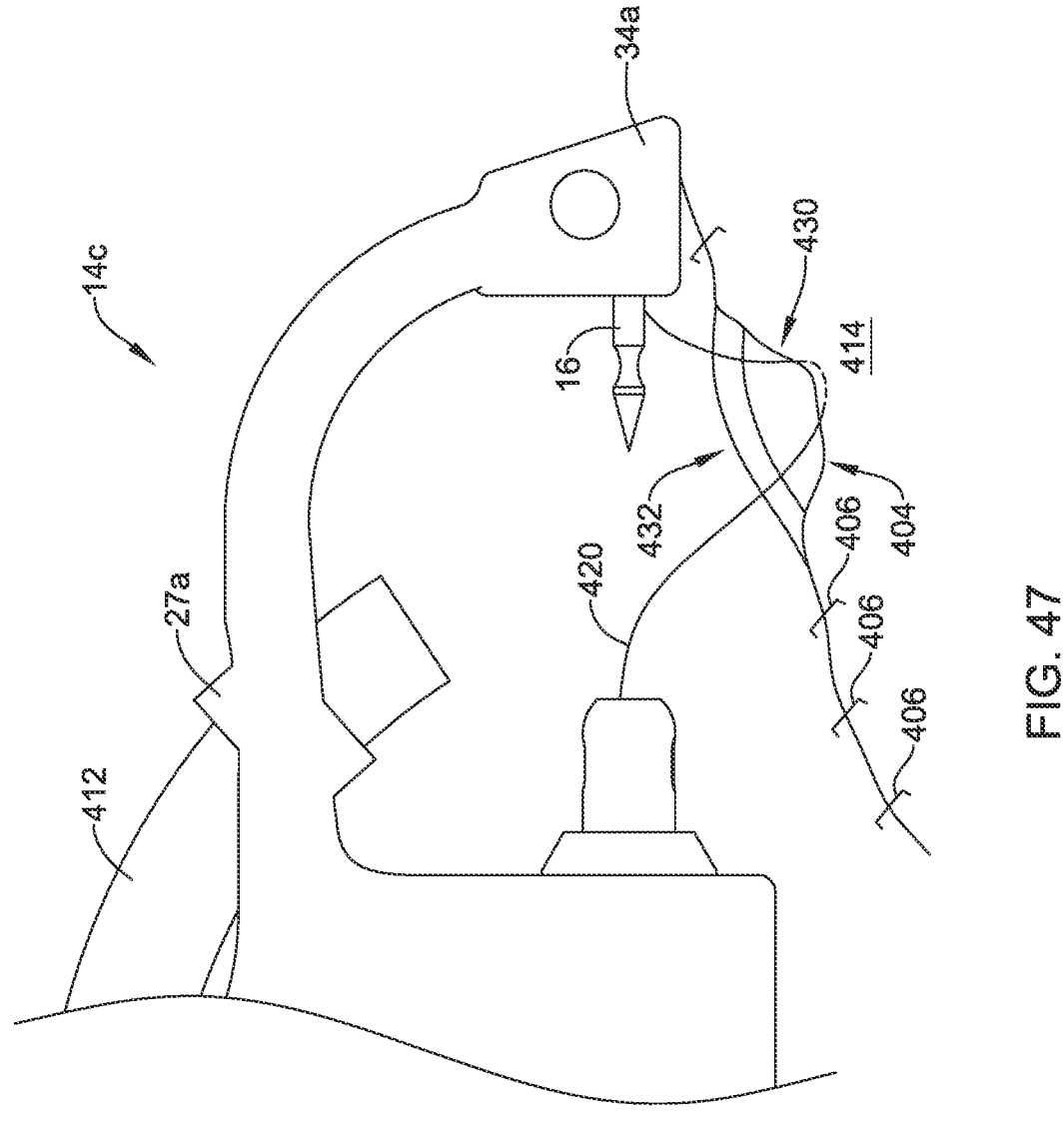

Starting in FIG. 44, the distal assembly 14*c* has been positioned relative to the defect 400. A tissue grasping tool 410 extends through a tubular member 412 that is secured relative to the guide structure 27*a*, and may be positioned such that the tissue grasping tool 410 is able to grasp tissue 414 proximate one side of the remaining open portion 404 of the defect 400, and the tissue 414 may be pulled upward by retracting the tissue grasping tool 410, as denoted by an arrow 416. As the tissue 414 is pulled upward, as noted in FIG. 45, suturing may begin. In FIG. 46, it can be seen that the needle 16 has been passed through the tissue 414 and has been grasped by the end cap 34*a*, thereby pulling a suture 420 through the tissue 414. As can be seen in FIG. 47, the suture 420 now extends through the tissue 414 on a first side 430 of the remaining open portion 404 of the defect 400. The suturing process may continue by repeating the aforementioned steps on the second side 432 of the remaining open portion 404 of the defect 400.

It will be appreciated that a variety of different materials may be used in forming the devices described herein. In some cases, a variety of different metals may be used. Illustrative but non-limiting examples of suitable metals include titanium, stainless steel, magnesium, cobalt chromium and others. In some embodiments, for example, the devices described herein may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A suture device comprising:
a needle configured to be coupled with a suture;
a distal shuttle configured to releasably engage the needle; and
a locking member axially slidably disposed over the distal shuttle to be actuated to move between a locked position in which the locking member secures the needle with respect to the distal shuttle, and an unlocked position in which the needle is releasable from being locked with respect to the locking member;
wherein the locking member comprises a sleeve configured to receive the distal shuttle and axially slidable over the distal shuttle.

2. The suture device of claim 1, wherein:
when in the locked position, the locking member holds locking elements radially inwardly with respect to the needle to lock the needle with respect to the distal shuttle; and
when in the unlocked position, the locking member is axially translated out of operable contact with the locking elements to allow the locking elements to move radially outwardly out of engagement with the needle to allow the needle to be moved with respect to the distal shuttle.

3. The suture device of claim 2, wherein the locking elements are separately movable with respect to the distal shuttle and the locking member.

4. The suture device of claim 2, wherein the locking elements are formed on the distal shuttle.

5. The suture device of claim 2, wherein the needle includes a proximal detent releasably engageable by the locking elements.

6. The suture device of claim 1, wherein, in the locked position, the locking member releasably engages locking elements engageable with the needle.

7. The suture device of claim 1, further comprising a control handle operably coupled with the locking member to axially move the locking member between the locked position and the unlocked position.

8. The suture device of claim 1, wherein the distal shuttle defines a distal needle opening configured to accommodate the needle and aligned with a longitudinal axis of the needle.

9. A suture device comprising:

a needle configured to be coupled with a suture;

a distal shuttle configured to releasably engage the needle in a locked position and to disengage the proximal detents of the needle in an unlocked position;

a locking member axially slidable with respect to the distal shuttle and comprising a sleeve configured to receive the distal shuttle and axially slidable over the distal shuttle; and a handle assembly including a proximal handle and a translating handle, the translating handle slidingly disposed distal to the proximal handle to axially translate the locking member with respect to the distal shuttle to move the distal shuttle between the locked position and the unlocked position.

10. The suture device of claim 9, wherein the translating handle is coupled to the locking member via a cable.

11. The suture device of claim 9, wherein the locking member is configured to releasably engage locking elements engageable with the needle.

12. The suture device of claim 9, further comprising an endcap distally spaced from the distal shuttle and configured to releasably engage the needle to hold the needle in a locked position.

13. A suture device comprising:

a needle configured to be coupled with a suture;

a distal shuttle configured to releasably engage the needle;

one or more locking elements radially movable with respect to the needle between an engaged position with the needle, in which axial movement of the needle with respect to the distal shuttle is inhibited, and an unengaged position with the needle in which axial movement of the needle with respect to the distal shuttle is uninhibited; and a locking member comprising a sleeve configured to receive the distal shuttle and axially slidable between a position engaging the one or more locking elements and a position unengaged with the one or more locking elements.

14. The suture device of claim 13, wherein the locking member is axially slidable with respect to the distal shuttle to move between a locked position in which the locking member secures the needle with respect to the distal shuttle, and an unlocked position in which the needle is releasable from being locked with respect to the locking member.

15. The suture device of claim 14, wherein:

when in the locked position, the locking member holds the one or more locking elements radially inwardly with respect to the needle to lock the needle with respect to the distal shuttle; and when in the unlocked position, the locking member is axially translated out of operable contact with the one or more locking elements to allow the one or more locking elements to move radially outwardly out of engagement with the needle to allow the needle to be moved with respect to the distal shuttle.

16. The suture device of claim 14, wherein the locking member engages the one or more locking elements when in the locked position to hold the one or more locking elements in position with respect to the distal shuttle.

17. The suture device of claim 13, wherein the one or more locking elements are separately movable with respect to the distal shuttle and the locking member.

18. The suture device of claim 13, wherein the one or more locking elements are formed on the distal shuttle.

19. The suture device of claim 13, wherein the needle includes a proximal detent releasably engageable by the one or more locking elements.

20. The suture device of claim 13, further comprising a control handle operably coupled with the locking member to axially move the locking member between the locked position and the unlocked position.

* * * * *